(12) United States Patent
Lockhart et al.

(10) Patent No.: US 11,762,466 B2
(45) Date of Patent: Sep. 19, 2023

(54) TREMOR DETECTING AND RENDERING IN VIRTUAL REALITY

(71) Applicant: PENUMBRA, INC., Alameda, CA (US)

(72) Inventors: Arthur John Lockhart, San Ramon, CA (US); Hans Peter Winold, Berkeley, CA (US); Andrew Taylor Langley, Alameda, CA (US); Colin Davies, Walnut Creek, CA (US); Seppo Helava, Oakland, CA (US)

(73) Assignee: Penumbra, Inc., Alameda, CA (US)

( * ) Notice: Subject to any disclaimer, the term of this patent is extended or adjusted under 35 U.S.C. 154(b) by 82 days.

(21) Appl. No.: 17/382,492

(22) Filed: Jul. 22, 2021

(65) Prior Publication Data
US 2022/0035452 A1 Feb. 3, 2022

Related U.S. Application Data

(60) Provisional application No. 63/057,990, filed on Jul. 29, 2020.

(51) Int. Cl.
*G06F 3/01* (2006.01)
*G06N 3/08* (2023.01)
(Continued)

(52) U.S. Cl.
CPC ............ *G06F 3/014* (2013.01); *A61B 5/1101* (2013.01); *G06N 3/08* (2013.01); *G06T 13/40* (2013.01)

(58) Field of Classification Search
CPC ....... A61B 5/744; A61B 5/486; A61B 5/1101; A61B 5/11; G06T 13/40;
(Continued)

(56) References Cited

U.S. PATENT DOCUMENTS

2004/0169620 A1* 9/2004 Baram ................... G16H 40/63
345/8
2014/0347392 A1 11/2014 Odessky et al.
(Continued)

OTHER PUBLICATIONS

"Expert team develops diagnostic system for Parkinson's patients," HRW (2 page) (2021).
(Continued)

*Primary Examiner* — Xilin Guo
(74) *Attorney, Agent, or Firm* — Haley Guiliano LLP

(57) ABSTRACT

Systems and methods are provided for measuring and identifying real-world tremors in order to calculate and display an anti-tremor in a virtual reality world. A system may identify a tremor in a body part, such as hands, and measure the tremor movement from, e.g., body sensors, to calculate an opposite movement and animate virtual hands performing the reverse tremor motion. Depicting inverse motions, such as an anti-tremor, may be used in a few ways to therapeutically train and exercise patients to better control their tremors. Providing a visual cue may help a patient interrupt the movement, as well as provide possibilities for therapy or training muscle memory and stimulating nerve and neuron
(Continued)

recovery. By displaying an anti-tremor with virtual hands, a VR system may be used to help train or exercise body parts experiencing tremors.

20 Claims, 13 Drawing Sheets

(51) Int. Cl.
*G06T 13/40* (2011.01)
*A61B 5/11* (2006.01)

(58) Field of Classification Search
CPC ... G06T 2219/2004; G06T 7/20; G06F 3/014; G06F 3/011; G06F 18/217; G06F 3/017; G06F 3/041; G06N 3/08; G06N 3/006; G06V 40/10; G06V 40/20
See application file for complete search history.

(56) References Cited

U.S. PATENT DOCUMENTS

| | | | | |
|---|---|---|---|---|
| 2018/0132756 | A1* | 5/2018 | Kording | A61B 5/4082 |
| 2019/0110754 | A1 | 4/2019 | Rao et al. | |
| 2020/0098339 | A1* | 3/2020 | Nandakumar | G06F 1/1694 |
| 2020/0281508 | A1* | 9/2020 | Ren | A61B 5/4519 |

OTHER PUBLICATIONS

Cikajo et al, "Advantages of using 3D virtual reality based training in persons with Parkinson's disease: a parallel study," Journal of NeuroEngineering and Rehabilitation, 16:119 14 pages) (2019).
Citroner, "How This Virtual Reality Program Can Help People with Parkinson's," Health News (12 pages) (2019).
Cornacchioli et al., "Virtual Reality Tremor Reduction in Parkinson's Disease," Preprints (8 pages) (2020).
Could virtual reality help improve balance in people with MS? (6 pages) (2016).
Fernandez-Gonzalez et al., "Leap Motion Controlled Video Game-Based Therapy for Upper Limb Rehabilitation for Parkinson," Journal of NeuroEngineering and Rehabilitation, 16(1):133 (2019).
Konforti, "VR Based Rehab System Has Promising Impacton Parkinson," (4 pages) (2016).
Lei et al., "Effects of virtual reality rehabilitation training on gait and balance in patients with Parkinson's disease: A systematic review," PLOS One, 14(11):e0224819 (2019).
Lopes, "Virtual Reality Game by Engineering Students May Help Parkinson's Patients with Walking," (6 pages) (2019).
PCT International Search Report for International Application No. PCT/US2021/042782, dated Oct. 26, 2021 (12 pages).

* cited by examiner

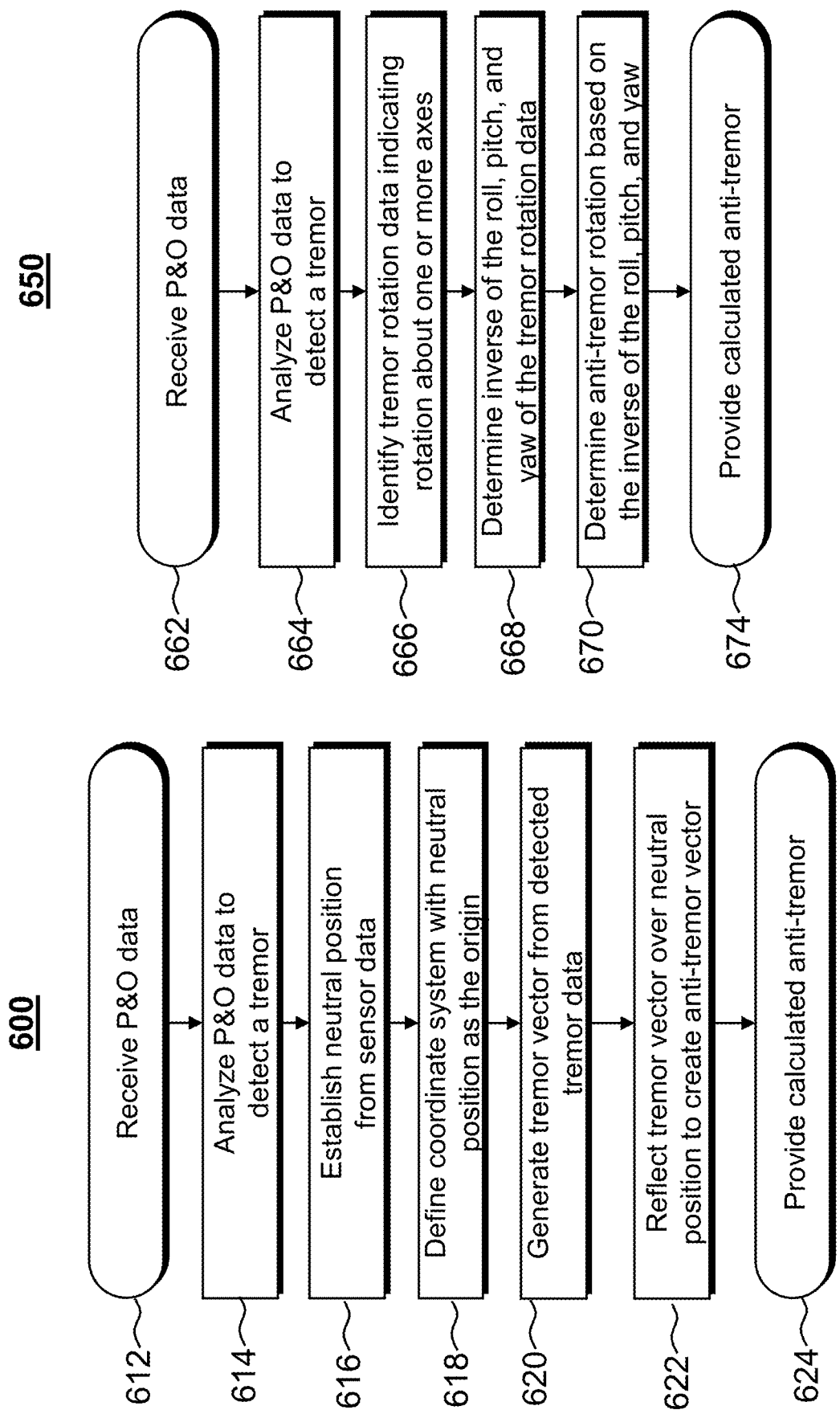

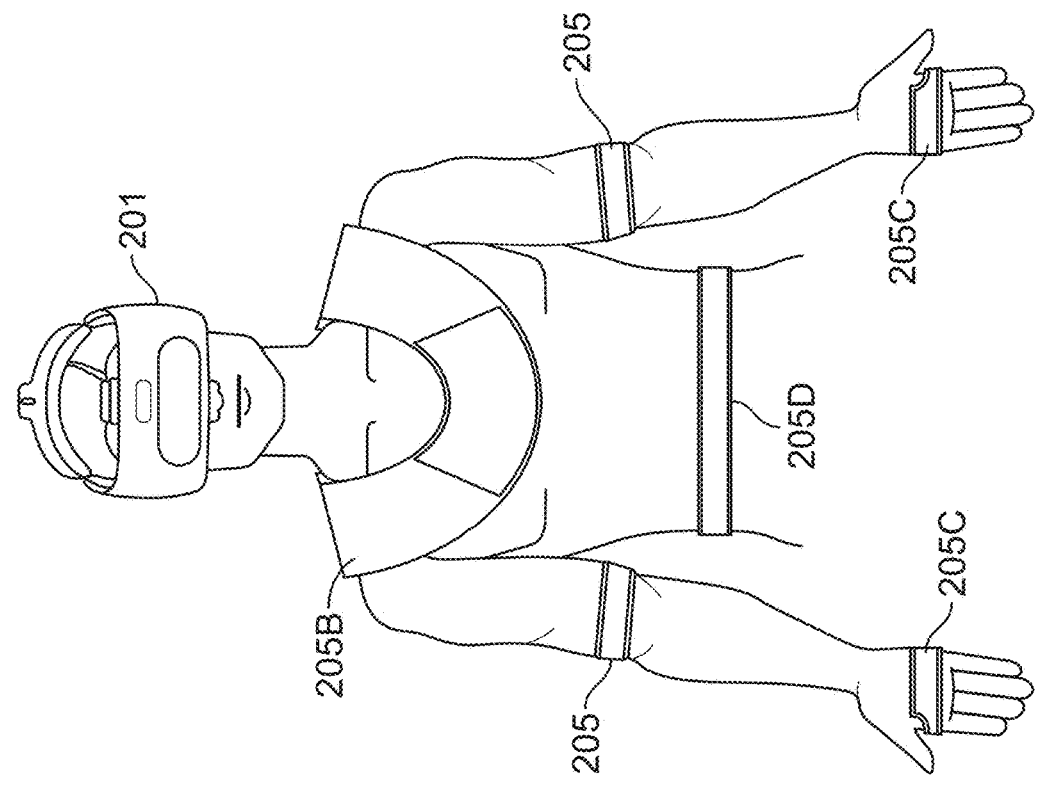
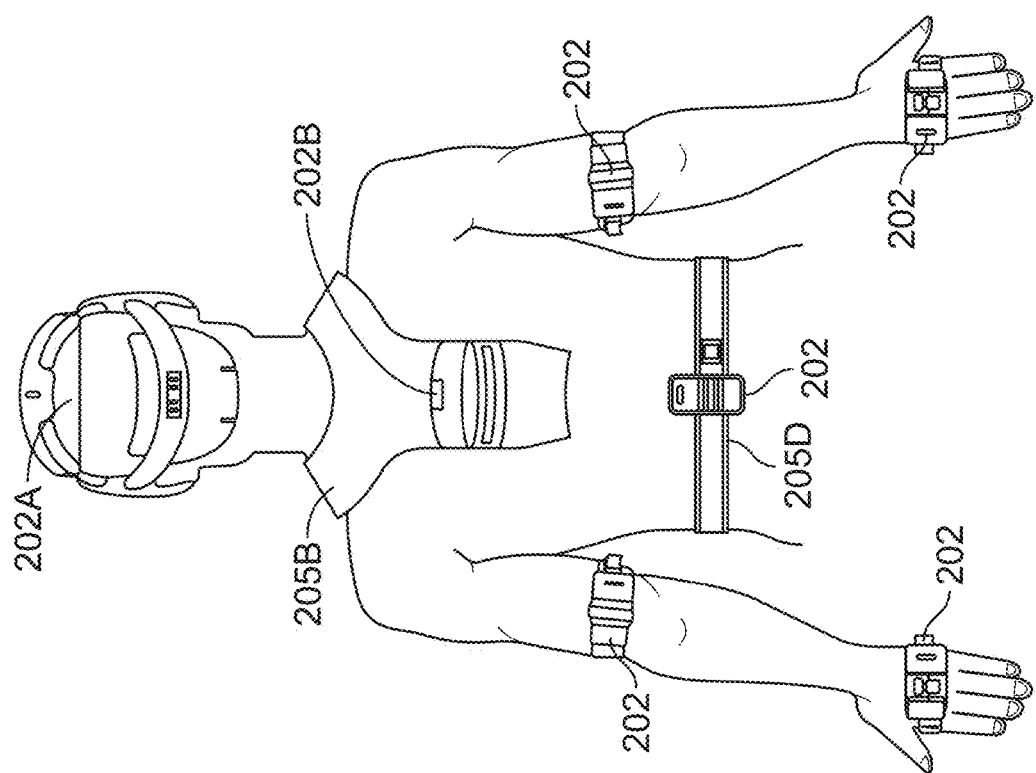
FIG. 7C

TREMOR DETECTING AND RENDERING IN VIRTUAL REALITY

CLAIM OF PRIORITY

This application is related to, and hereby claims the benefit of, U.S. Provisional Patent Application No. 63/057,990, filed Jul. 29, 2020, which is hereby incorporated by reference herein in its entirety.

BACKGROUND OF THE DISCLOSURE

The present disclosure relates generally to virtual reality systems and more particularly to animating an avatar of a patient experiencing involuntary body movements such as tremors.

SUMMARY OF THE DISCLOSURE

Virtual reality systems may be used in various applications, including therapeutic activities and games, to assist patients with their rehabilitation and recovery from illness or injury. VR may be used to monitor and help patients retrain their brains and muscles to perform certain tasks that may be difficult in a safe, observable environment. Movement disorders may cause uncontrolled muscle movements, such as tremors, that may make common tasks difficult.

A tremor may be considered any common movement disorder and, for instance, may be characterized by an involuntary, rhythmic muscle contraction causing shaking. Tremors are common in the hands but may also occur in other body parts such as arms, head, vocal cords, torso, or legs. Disorders such as Parkinson's disease may cause tremors in one or more body parts. As discussed herein, VR systems may be used in therapy to detect, measure, and animate uncontrolled muscle movements, such as hand tremors, in a virtual reality world. While hand tremors may be used as an example, such a system may be applicable to other body parts that may experience uncontrolled movements and/or tremors caused by various movement disorders.

Generally, VR systems can be used to instruct users in their movements while therapeutic VR can recreate practical exercises that may further rehabilitative goals such as physical development and neurorehabilitation. For instance, patients with movement disorders may use physical therapy for treatment to improve, e.g., range of motion, balance, coordination, mobility, flexibility, posture, endurance, and strength. Physical therapy may also help with pain management. Physical therapy may help patients with movement disorders develop physically and mentally to better perform everyday living functions. VR systems can depict avatars performing actions that a patient with involuntary movements may not be able to fully execute.

In a virtual universe, movements beyond what is normally physically performed may be possible. A VR system may use an avatar of the patient and animate the avatar in the virtual world. Using sensors in VR implementations of therapy allows for real-world data collection as the sensors can capture movements of body parts such as hands and arms for the system to convert and animate an avatar in a virtual environment. Such an approach may approximate the real-world movements of a patient to a high degree of accuracy in virtual-world movements. Data from the many sensors may be able to produce statistical feedback for viewing and analysis by doctors and therapists. Generally, avatar animations in a virtual world may closely mimic the real-world movements, but virtual movements may be exaggerated and modified in order to aid in therapeutic activities. Visualization of patient movements through avatar animation could stimulate and promote neuron repairs, recovery and regeneration for the patient.

As one example, a virtual world avatar may directly mimic involuntary movements of a patient and demonstrate movements of a tremor in the virtual world. Seeing the replicated tremor in the avatar, a patient may attempt to stabilize or halt the tremor's shaking. In the physical world, a patient may not be able to control the shaking and may not understand how to stabilize the tremor. However, in the virtual environment, a patient could consciously and/or subconsciously work to counteract the tremor movements displayed by the avatar. Such attempts and efforts by the patient could stimulate muscle control and associated neuron repairs, recovery, and regeneration in the patient's neuro and muscular networks.

As another example, animations of a VR avatar may eliminate all involuntary motion of a patient and perform movements without any tremor in the virtual world. Such an approach may be valuable to the patient seeing her avatar's hand not shaking temporarily, but eliminating tremor animations may not help a patient recognize when she is experiencing tremors and what she can do physically during the tremors. There exists a need to demonstrate, to patients, ways to move their body parts to potentially reduce the physical manifestations of tremors.

As disclosed herein, a VR system may be configured to demonstrate movements by an avatar that may therapeutically aid a patient in coping with tremors in the physical world. Modes of VR can demonstrate avatar body movements during a tremor that may be used to instruct and exercise patients with movement disorders. An "anti-tremor" mode of a VR system may depict an avatar with a tremor with, e.g., an inverse motion in order to teach the patient to perform movements that may be used to reduce the tremor in the real world. An "anti-tremor" may be considered to be an inverse oscillation of a body part experiencing a tremor used for training and therapy. Disclosed herein, are several ways to detect and measure tremors in order to calculate and depict a functional anti-tremor within a VR system.

A VR system may be configured to measure and identify real-world tremors in order to calculate and display an anti-tremor in the virtual world. A system may identify a tremor in a body part, such as hands, and measure the tremor movement to calculate an opposite movement in order to animate virtual hands performing the reverse motion. Depicting inverse motions, such as an anti-tremor, may be used in a few ways to therapeutically train and exercise patients to better control their tremors. Providing a visual cue may help a patient interrupt the movement, as well as provide possibilities for therapy or training muscle memory and stimulating nerve and neuron recovery.

For instance, a VR therapy session may utilize an anti-tremor mode that can be toggled on or off. When anti-tremor mode is turned off, normal movements are depicted in the virtual world, but when anti-tremor mode is turned on, the system identifies tremors and depicts avatar movements with reverse motions. By displaying an anti-tremor with virtual hands, a VR system may be used to help train or exercise body parts experiencing tremors. Observing anti-tremors in virtual training or therapy may allow a patient to become more aware of how his body parts tremor. For example, an individual with Parkinson's disease may not be able to control his tremors but may be able to alter movements of a body part experiencing tremors when viewing a virtual avatar in a VR system. In the real world, a patient may see his hand physically tremor and try to steady the hand by resisting the movement. Using VR systems, patients with movement disorders may experience their involuntary movements differently. If a patient views uncontrolled motion as an anti-tremor in the virtual world and is directed to consciously mimic the animated (reverse) movements, a patient may be able to minimize or control the manifestations of a tremor. Patients may find it easier to match an observed movement than to perform the opposite. Perhaps just as importantly, using the raw sensor data, the system may measure the tremors and the movements with the goals of logging data to show progress in physical movement and tremor control.

In order to accomplish animating an anti-tremor, a VR system must analyze data from physical sensors to identify a tremor as it occurs. Tremors are typically seen as small repetitive movements. VR system sensors may measure these movements, for instance, in six degrees of movement on a three-dimensional cartesian axis and three rotational axes. As patients with tremors are monitored and data is collected, a neural network may be trained to identify tremors. A VR system may implement an artificial intelligence to discern sensor data indicating a tremor from other movements and/or sensor noise.

Once a tremor is detected, calculating an anti-tremor may be accomplished in several ways. Generally, a VR system may be configured to convert real world coordinates into virtual world coordinates in order to, e.g., convert real world movements to avatar movements. An anti-tremor in avatar movement may generally be depicted as inverted motion by, e.g., transforming one or more sensor's coordinates around a neutral position of a body part experiencing the tremor. When the system is not in anti-tremor mode, the VR system collects raw sensor data, filters the raw data, passes the filtered data to an inverse kinematics (IK) engine, then the avatar solver generates a skeleton and mesh and the solver renders the avatar. In anti-tremor mode the sensor data for a tremor must be converted to anti-tremor data at some point between sensor collection and avatar animation. For instance, if the anti-tremor mode is turned on, the system detects a tremor, and converts the data describing the tremor to an anti-tremor and passes the anti-tremor data to the IK engine. Alternatively, while in anti-tremor mode, the system may detect a tremor, pass the tremor data to the IK engine, and convert the data describing the tremor to an anti-tremor.

If a tremor is detected, and anti-tremor to be calculated, while the body part is moving, a neutral baseline position may be changing throughout the tremor. For instance, a patient might experience a tremor while performing a task of lifting an object within an activity designed to help a patient practice to offset a tremor and anti-tremor mode must invert the tremor while depicting the hand moving vertically.

Animating an anti-tremor motion may be performed in a similar manner to animating motion normally in a VR system. Once the IK engine has the proper data to animate the avatar, animating an anti-tremor motion may be performed in a similar manner to animating motion normally in a VR system.

BRIEF DESCRIPTION OF THE DRAWINGS

The above and other objects and advantages of the disclosure will be apparent upon consideration of the following detailed description, taken in conjunction with the accompanying drawings, in which like reference characters refer to like parts throughout, and in which:

FIG. 6A depicts an illustrative flowchart of a process for generating an anti-tremor, in accordance with some embodiments of the disclosure;

FIG. 6B depicts an illustrative flowchart of a process for generating an anti-tremor, in accordance with some embodiments of the disclosure;

FIG. 7C is a diagram of an illustrative system, in accordance with some embodiments of the disclosure;

DETAILED DESCRIPTION

Figure 1:
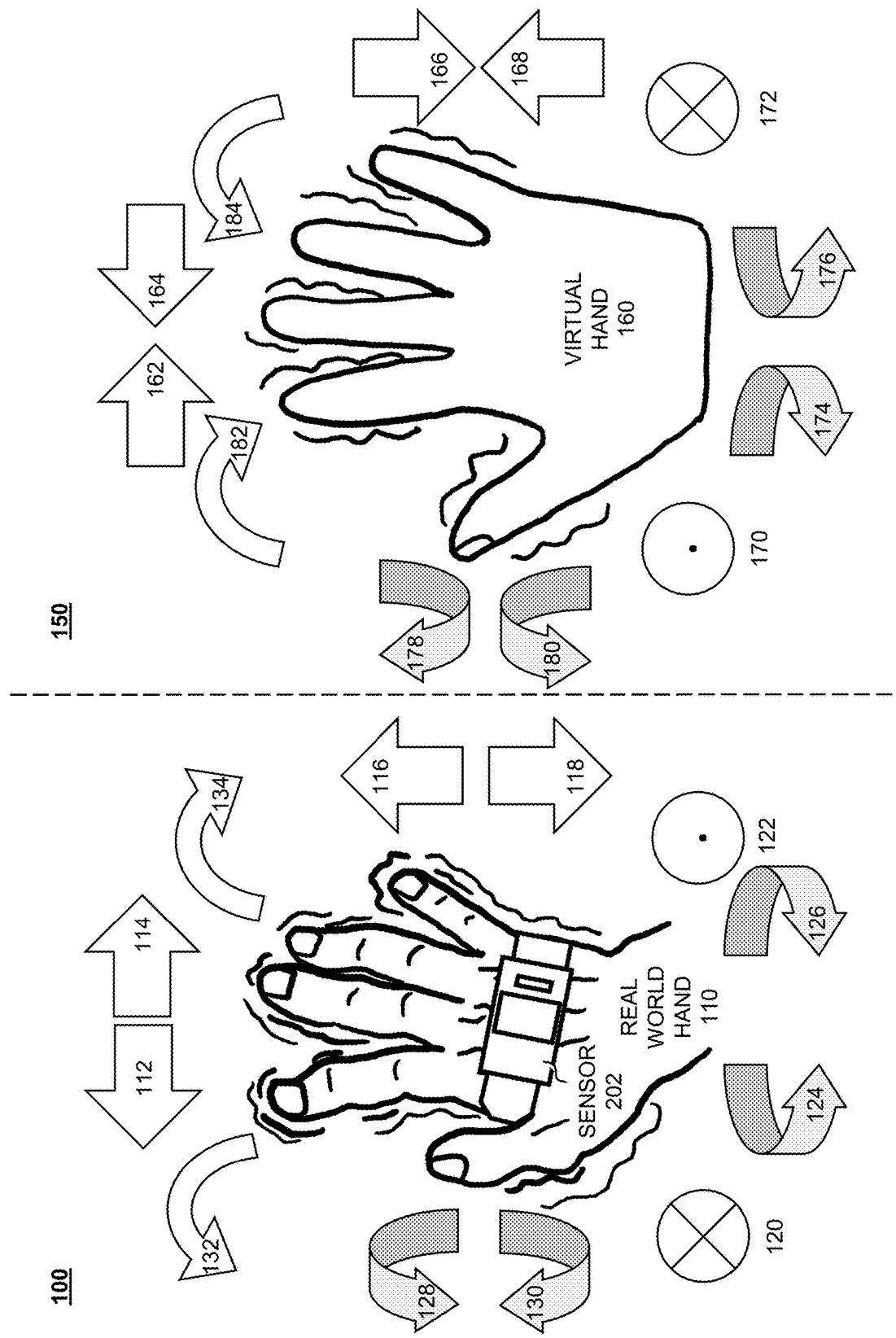
FIG. 1 is an illustrative depiction of hand tremor movement and an avatar exhibiting anti-tremor movements, in accordance with some embodiments of the disclosure.

FIG. 1 is an illustrative depiction of hand tremor movement and an avatar exhibiting anti-tremor movements, in accordance with some embodiments of the disclosure. For instance, scenario 100 of FIG. 1 depicts various potential movements of a patient's hand in the real world, e.g., real-world hand 110, in six degrees of freedom. Scenario 150 of FIG. 1 depicts various potential movements of an avatar's hand in the virtual world, e.g., virtual hand 160, in six degrees of freedom. Generally, a virtual hand is depicted to mimic the motions of a real hand, however, FIG. 1 illustrates how virtual hand 160 may depict motions of an anti-tremor than are in inverse to motions of real-world hand 110. As disclosed further below, scenario 150 may be provided during an "anti-tremor" mode of a VR system animating an avatar with a tremor that is inverted movements (e.g., opposite or reverse) to the motions in scenario 100, potentially used in VR physical therapy, exercise, and/or training.

Real-world hand 110 is shown wearing sensor 202, as part of an exemplary VR system such as the systems and devices depicted in FIGS. 7-10. Wireless sensor module 202 (e.g., sensor or WSM) may be worn as strapped to the back of one or more hands. Sensor 202 is equipped with mechanical and electrical components that measure position and orientation in physical space to be translated for creating a virtual environment. In some embodiments, multiple sensors 202 may be placed on a patient, for example, just above each elbow, strapped to the back of each hand, and at the pelvis, as well as sensors placed on the back and in a head-mounted display (HMD).

Sensor 202 may track movement along six degrees of freedom. Involuntary movements, such as tremors, may be measured in one or more of the six degrees of movement for translation and depiction in a virtual world. Scenario 100 depicts six degrees of movement in arrows 112-132. For instance, arrow 112 indicates movement to the left on the x-axis, while arrow 114 indicates movement to the right on the x-axis. Arrow 116 indicates movement forward on the y-axis, while arrow 118 indicates movement backwards on the y-axis. Arrow 120 indicates downward movement on the z-axis, while arrow 122 indicates upward movement on the z-axis. Arrow 124 indicates tilting movement to the right around the roll axis, while arrow 126 indicates tilting movement to the left on the roll axis. Arrow 128 indicates backward tilting movement around the pitch axis, while arrow 130 indicates forward tilting movement on the pitch axis. Arrow 132 indicates tilting movement to the left around the yaw axis, while arrow 134 indicates tilting movement to the right on the yaw axis. Sensor 202 may measure movements in one or more of these directions for translation into avatar movement in a virtual world.

Virtual hand 160 is shown with arrows 162-182 indicating inverse movements of counterpart motions, e.g., arrows 112-132, as depicted in scenario 100. For instance, arrow 162 of scenario 150 indicates avatar movement to the right on the x-axis, while arrow 112 of scenario 100 indicates real-world movement to the left on the x-axis. Arrow 164 indicates avatar movement to the left on the x-axis, while arrow 114 indicates real-world movement to the right on the x-axis. Arrow 166 of scenario 150 indicates avatar movement backward on the y-axis, while arrow 116 of scenario 100 indicates real-world movement forward on the y-axis. Arrow 168 indicates avatar movement forward on the y-axis, while arrow 118 indicates real-world movement backward on the y-axis. Arrow 170 indicates upward movement by the avatar on the z-axis, while arrow 120 indicates downward real-world movement on the z-axis. Arrow 172 indicates downward movement by the avatar on the z-axis, while arrow 122 indicates upward real-world movement on the z-axis. Arrow 174 indicates avatar tilting movement to the left on the roll axis, while arrow 124 indicates real-world tilting movement to the right around the roll axis. Arrow 176 indicates avatar tilting movement to the right on the roll axis, while arrow 126 indicates tilting real-world movement to the left on the roll axis. Arrow 178 indicates forward tilting avatar movement on the pitch axis, while arrow 128 indicates backward tilting real-world movement around the pitch axis. Arrow 180 indicates backward tilting avatar movement on the pitch axis, while arrow 130 indicates forward tilting real-world movement on the pitch axis. Arrow 182 indicates avatar tilting movement to the right on the yaw axis, while arrow 132 indicates real-world tilting movement to the left around the yaw axis. Arrow 184 indicates avatar tilting movement to the left on the yaw axis, while arrow 134 indicates real-world tilting movement to the right on the yaw axis.

By rendering on or more motions of virtual hand 160 as opposites of the movements of real-world hand 110, an "anti-tremor" mode may be established that animates a VR avatar performing opposite movements while the patient experiences a tremor. Such an "anti-tremor" mode of a VR system may depict an avatar with an anti-tremor in order to teach the patient to perform movements that may be used to reduce the tremor in the real world. Seeing these anti-tremors, a patient may passively adopt motions that may help control or cancel out tremors they are experiencing in the real world.

Figure 2:
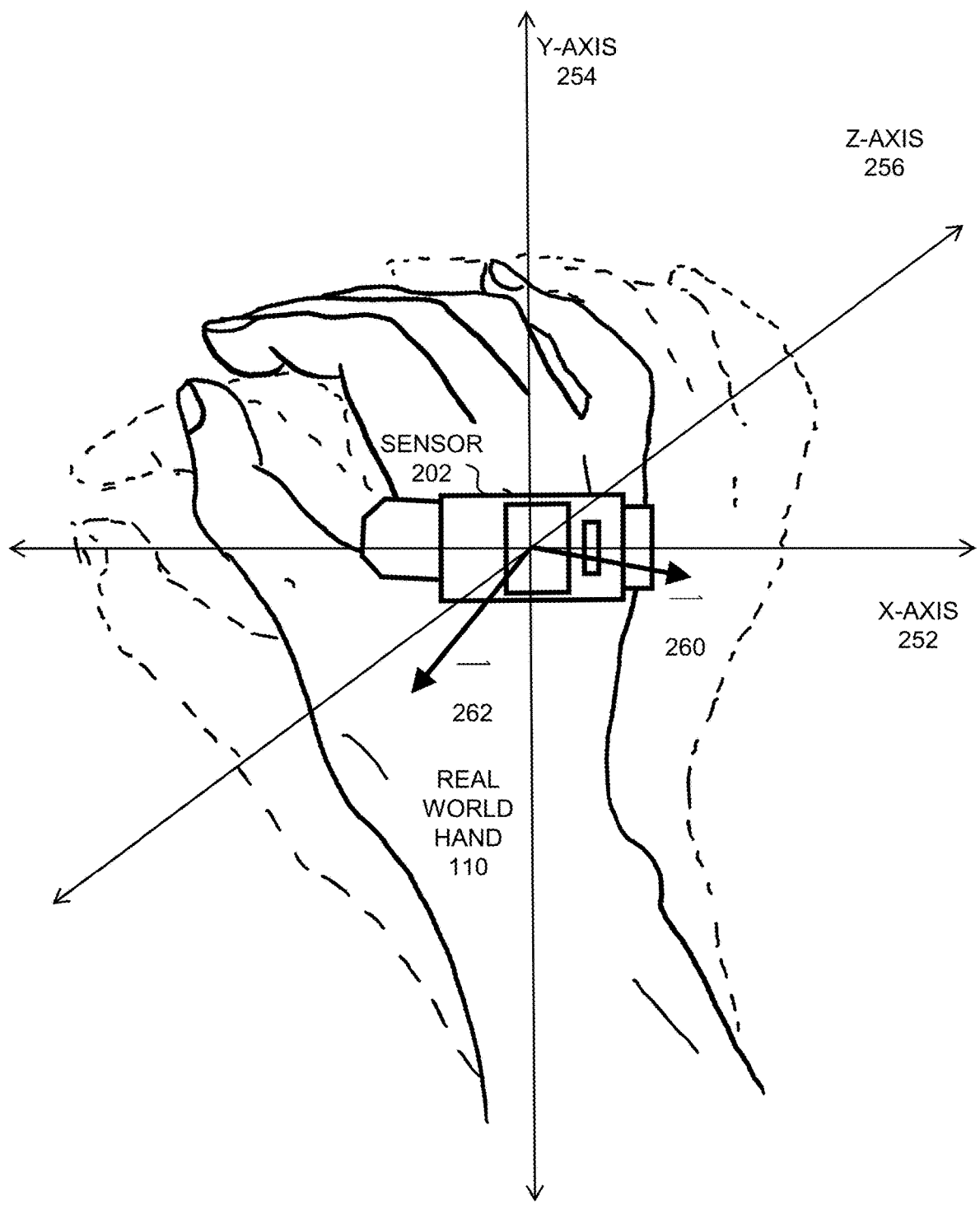
FIG. 2 depicts an illustrative setup for detecting and measuring movement caused by hand tremors, in accordance with some embodiments of the disclosure.

FIG. 2 depicts an illustrative setup for detecting and measuring movement caused by hand tremors, in accordance with some embodiments of the disclosure. Scenario 200 of FIG. 2 depicts real-world hand 110 wearing sensor 202 as part of an exemplary VR system such as the systems and devices depicted in FIGS. 7-10. Sensor 202 is depicted on a set of axes, e.g., axes 252-256, with an origin at the center of sensor 202. Sensor 202 can measure movement in six degrees of freedom.

Scenario 200 depicts involuntary movement in the form of a tremor. Tremor movement may be measured, e.g., as a vector, in one or more of the three axes. Tremor rotational movement may be measured around one or more of the three axes with an origin set to a neutral state. In some embodiments, a set of axes may be set around a sensor at a determined neutral state. In some embodiments, sensor data may be determined based on physical offsets from other sensors or VR equipment and coordinates established based on relative position of a neutral state. In some embodiments, when a tremor is detected, sensor 202 may provide position and orientation data to be converted to coordinates of axes set around a sensor. In some embodiments position and orientation data may be used to measure movement to be converted as an anti-tremor movement When translating coordinate systems for animation, each individual vertex of a polygon mesh may contain position information, orientation information, weight information, and other information. The vertices may be defined as vectors within a Cartesian coordinate system, whereby each vertex has a corresponding (x, y, z) position in cartesian space. In some embodiments, the virtual bone transformations may be defined as vectors in Quaternion space, whereby each bone has a corresponding (l, i, k, j) position in quaternion space. Quaternion representation of rotation for bone transformations beneficially avoids gimbal locks that temporarily reduces a tracked object's degrees of freedom. Gimbal lock is associated with tracking, and, thus, animation errors.

In scenario 200, tremor movement may be measured as a vector in three-dimensional space, with components along x-axis 252, y-axis 254, and z-axis 256. Real-world hand 110 may be thought of as oscillating between the right-most dotted lines and the left-most doted lines. For instance, displacement vector 260, $\vec{D_1}$, represents displacement of real-world hand 110 in the coordinate system of scenario 200 as real-world hand moved to the right-most position. Displacement vector 262, $\vec{D_2}$, represents displacement of real-world hand 110 in the coordinate system of scenario 200 as real-world hand moved to the left-most position.

In some embodiments, a VR system may be in an anti-tremor mode and may determine an anti-tremor displacement vector based on an inversion of a displacement vector, e.g., $\vec{D_1}$ or $\vec{D_2}$. An inversion may appear as a reflection of a displacement vector over one or more axes. For instance, if $\vec{D_1}$ is written as (5, −1, 2) then an anti-tremor displacement of $\vec{D_1}$ may be determined to be (−5, 1, −2).

In some embodiments, a tremor may be recognized as a wave, e.g., by its periodicity and direction of motion. In some embodiments, a Discrete Fourier Transformation (DFT) may be used to identify tremors (or even a type of tremor, such as one caused by Parkinson's disease). For instance, in some embodiments, a system may determine periodicity of a hand tremor, and then sample the orientation at the midpoint of each period. In such an embodiment, by applying the determined midpoint of the tremor to an avatar hand in a virtual rendering, the tremor may be ignored completely, or an anti-tremor may be produced by inverting the wave. Such an approach may cause an avatar hand to react a little slowly to broader movement, but it could effectively filter out tremor-related movement while keeping gross movement. For instance, if tremors caused by Parkinson's disease are, e.g., around 4-7 Hz, larger movements would not be determined to be tremors, but changing the midpoint (e.g., neutral position) as an arm moves may not be realized quickly. In some embodiments, once a neutral position is determined, an approach using tremor removal through smart discrete selection rather than through additive correction may be computationally more efficient, as well.

Figure 3:
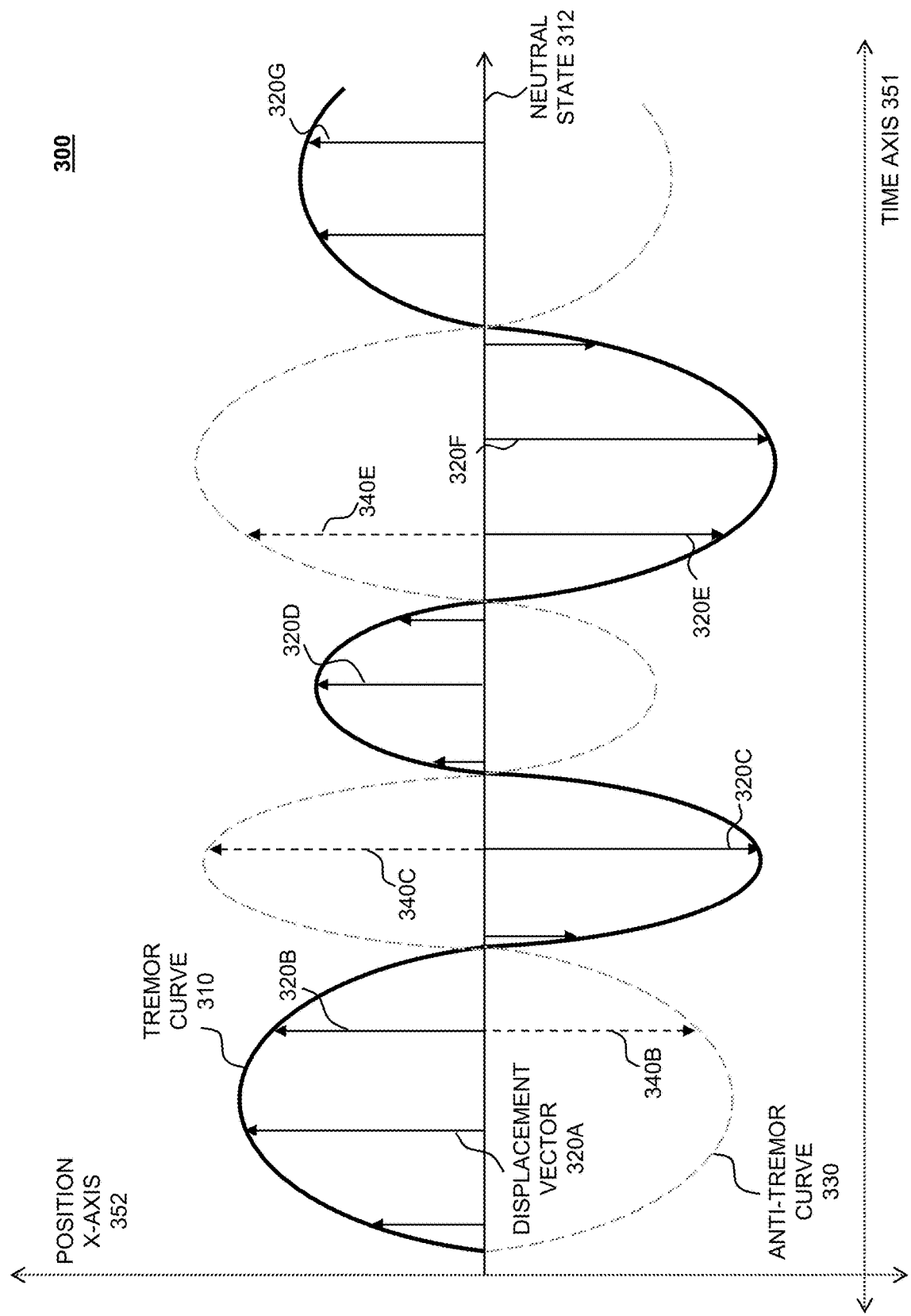
FIG. 3 depicts an illustrative graph for measuring movement caused by hand tremors, in accordance with some embodiments of the disclosure.

FIG. 3 depicts an illustrative graph for measuring movement caused by hand tremors, in accordance with some embodiments of the disclosure. FIG. 3 includes graph 300 which depicts a position on the x-axis 352 versus a time axis 351. Graph 300 features position x-axis 352 as measured by a sensor, e.g., sensor 202, but any position axis may yield similar readings, such as each of axes 252-256 of FIG. 2. Graph 300 depicts a component of a measured position in the x-axis that, when combined with measurements in other dimensions, produces a multi-dimensional position measurement. Positions may be measured by a sensor at regular intervals, e.g., 5 Hz, 30 Hz, 80 Hz, 200 Hz, or other frequencies. In some embodiments, sensor measurements may be filtered before transmitted and/or analyzed. Analyzing position measurements, e.g., during a tremor, an oscillation may appear on a given axis.

Plotted on graph 300 is a line representing neutral state 312, a measured sensor position if, e.g., the body part was not experiencing a tremor. For instance, neutral state 312 may be considered to be a position of a hand at rest without a tremor. In some embodiments, neutral state 312 may be calculated based on a weighted average of recent position measurements. In some embodiments, neutral state 312 may be extrapolated or interpolated from measurements of oscillation. In some embodiments, neutral state 312 may be identified from measurements of change in acceleration. In some embodiments, neutral state 312 may be measured and adjusted recursively as displacements of maximum and minimum amplitude may be measured. In some embodiments, neutral state 312 may be passed to an IK engine to render and animate an avatar experiencing no tremors.

Graph 300 includes illustrative displacement vectors 320A-G. Each displacement vector may be a relative measurement of sensor position on an axis in comparison to neutral state 312. Each position measurement may be taken and compared to a neutral state 312. For example, displacement vector 320A indicates movement away from the neutral state in a positive direction, e.g., right. Displacement vector 320B indicates movement on the positive (e.g., right) side of the neutral state but with a smaller magnitude than displacement vector 320A. Between displacement vectors 320A and 320B, in graph 300, tremor curve 310 peaked. Displacement vector 320C indicates movement away from the neutral state in a negative direction, e.g., left. Between displacement vectors 320B and 320C, in graph 300, tremor curve 310 passed through neutral state 312. As more measurements are taken over time, more displacement vectors may be calculated and a tremor curve 310 can be readily identified. In graph 300, exemplary tremor curve 310, based on sensor position measurements on the x-axis over time, appears as sinusoidal in shape. In some embodiments, e.g., depending on sensor capture frequency, tremor curve 310 may be produced by many measurements. In some embodiments, tremor curve 310 may extrapolated based on sensor measurements.

For each displacement vector, e.g., displacement vectors 320A-G, an inverse vector, may be determined. For instance, an inverse vector may be equal in magnitude to a displacement vector but opposite in direction. If a displacement vector is directed to the left, the inverse vector is directed to the right. A sum of inverse vectors on each axis (components) produces an inverse displacement vector at a given time, indicating the movement opposite to the tremor motion. If a tremor causes displacement in one direction on an axis, displacement in the opposite direction, at the same magnitude makes up an anti-tremor.

In graph 300, inverse vector 340B is the same magnitude and opposite direction (left) of displacement vector 320B (right). Inverse vector 340C is the same magnitude and opposite direction (right) of displacement vector 320C (left). Inverse vector 340E is the same magnitude and opposite direction (right) of displacement vector 320E (left). By plotting inverse vectors such as inverse vectors 340B, 340C, and 340E, anti-tremor curve 330 may be produced.

Graph 300 depicts exemplary anti-tremor curve 330 which is opposite to tremor curve 310. In some embodiments, anti-tremor curve 330 may be considered equal in frequency and opposite in amplitude to tremor curve 310. An "anti-tremor" may be considered an inverse oscillation of a body part experiencing a tremor used for training and therapy.

From determining an anti-tremor curve in each axis, a VR system may render avatar movement of a body part experiencing a tremor that matches the tremor but is opposite in direction. Anti-tremor data may be substituted for tremor data as the data is passed to an inverse kinematics engine for rendering and animation of an avatar. During a VR experience in "anti-tremor" mode, a patient experiencing tremors may see an anti-tremor in the avatar and may passively adopt motions that may help cancel out the tremor they are experiencing in the real world. Likewise, mimicking an anti-tremor in a virtual world may facilitate physical and mental control over a body part experiencing tremors. Using tremor data collected from sensors and anti-tremor calculations, movement data may be used in therapy, training, and exercise.

In some embodiments, sensor position and orientation data must be interpolated. For example, Fast Fourier Transform (FFT) algorithms may require regular intervals for datapoints, such as a three-dimensional position measurement every 0.05 seconds. In some embodiments, sensor capture intervals vary slightly and interpolation can resample the data to produce interpolated measurements at exact intervals to be transformed via FFT. For instance, a sensor may relay position and orientation data at varying intervals depending on an amount of movement, e.g., in order to use battery and transmission resources more efficiently. In such a case, each of the x, y, and z components may be plotted on a graph and, using an accelerometer on the sensor to measure and relay acceleration data, a smooth curve may be interpolated. In some embodiments, a script using Akima's interpolation method, e.g., Akima1DInterpolator, may be used to generate a smooth curve based on one-dimensional position data captured at varied intervals with sensor accelerometer data. For example, a smooth curve may appear like tremor curve 310 of FIG. 3, where displacement vectors 320A-G are taken at a regular interval (e.g., 0.05 sec). Such a curve may be re-sampled at an exact interval and input into the FFT algorithm.

In some embodiments, when interpolated sensor data (or regularly measured sensor data) for one dimension is input into a FFT algorithm, a Fourier series may be generated from the curve and used to identify a frequency of the tremor, e.g., where the transformed function reaches a local maximum over 3.0 Hz. In some embodiments, a Fourier series generated from a positional curve may be isolated to only a sinusoidal curve corresponding to, e.g., the identified frequency. Then, in some embodiments, the isolated positional curve may be input through an inverse Fourier transform to generate a curve indicating isolated tremor movement. This process may be performed for each dimension (e.g., x, y, and z) independently and then, for example, combined to create a 3-dimentsional tremor curve depicting frequency, amplitude, and one or more axes of isolated (tremor) motion.

Figure 4:
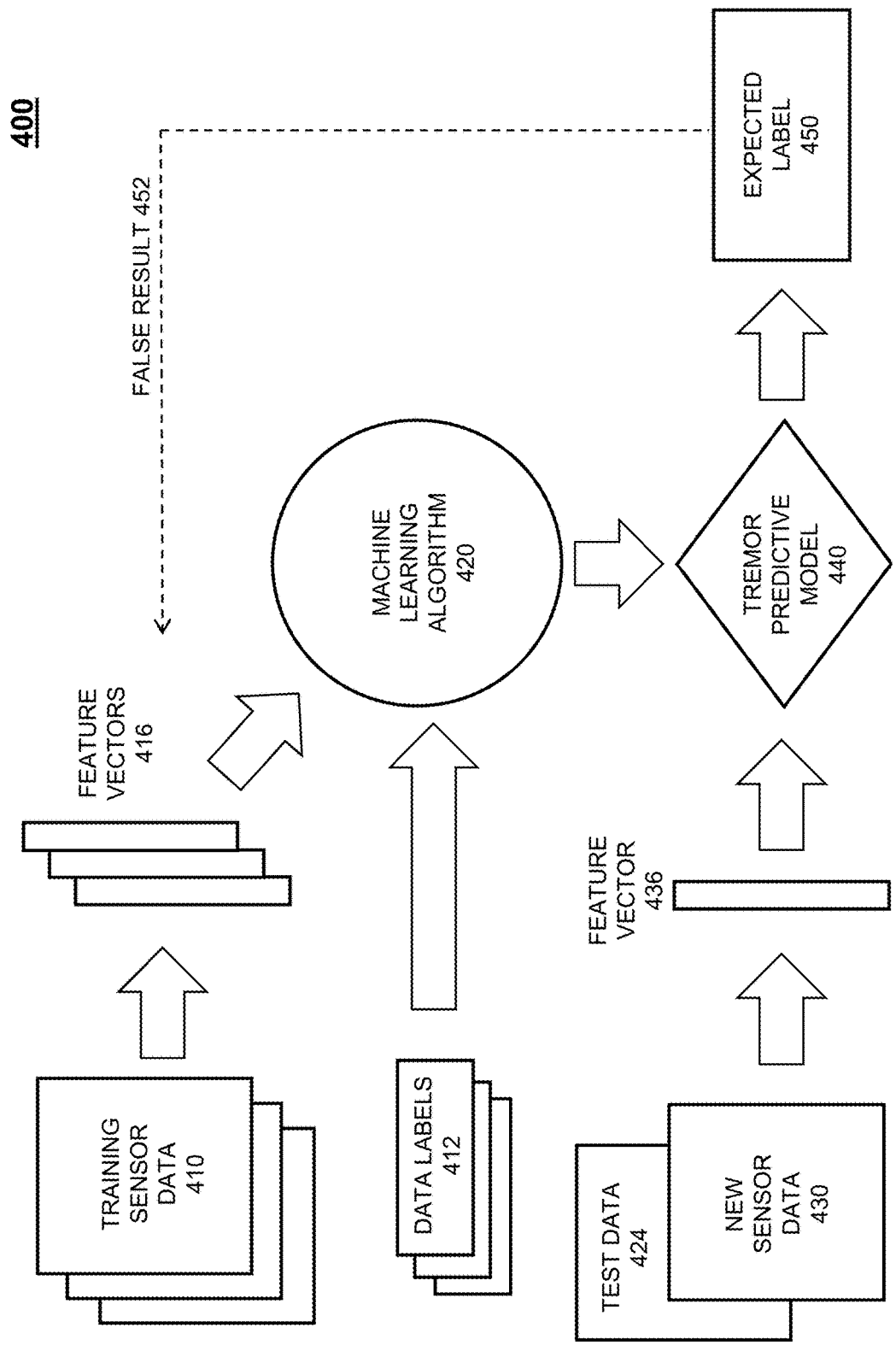
FIG. 4 depicts an illustrative flow diagram of a process for training a machine learning model to detect tremors in sensor data, in accordance with some embodiments of the disclosure.

FIG. 4 depicts an illustrative flow diagram of a process for training a machine learning model to detect tremors in sensor data, in accordance with some embodiments of the disclosure. In some embodiments, detecting a tremor may be accomplished with predictive modeling. For instance, a trained neural network may be used to classify provided sensor data as either a tremor or not a tremor. Generally, a training set comprising sensor data with tremors may be used by a neural network to predict if new sensor data includes a tremor or not.

Training a neural network to accurately detect tremors may be accomplished in many ways. Some embodiments may use supervised learning where, e.g., a training data set includes labels identifying tremors (and/or non-tremors). Some embodiments may use unsupervised learning that may identify tremors in training data by clustering similar data. Some embodiments may use semi-supervised learning where a portion of labeled sensor data may be combined with unlabeled data during training. In some embodiments, a reinforcement learning may be used. With reinforcement learning, a predictive model is trained from a series of actions by maximizing a "reward function," via rewarding correct labeling and penalizing improper labeling. Scenario 400 includes data labels 412, indicating a supervised or semi-supervised learning situation.

Scenario 400 depicts training sensor data 410 along with data labels 412. Training data for tremor identification may be collected by asking patients suffering from movement disorder to participate in data collection. For instance, several patients with Parkinson's disease may be asked to use the virtual reality system while sensor data is captured. Sensor data from a control group may also be captured. In some circumstances, a therapist or analyst may mark incoming data with a tremor or non-tremor label. From the sensor data collected, at least two groups of data may be created: training sensor data 410 and test data 424.

In scenario 400, training sensor data 410 is pre-processed using feature extraction to form training feature vectors 416. Pre-processing of training data is used to obtain proper data for training. In some embodiments, pre-processing may involve, for example, scaling, translating, rotating, converting, normalizing, changing of bases, and/or translating coordinate systems in sensor data. In some embodiments, pre-processing may involve filtering sensor data, e.g., to eliminate sensor noise.

After pre-processing, training feature vectors 416 are fed into Machine Learning Algorithm (MLA) 420 to generate an initial machine learning model, e.g., tremor predictive model 440. In some embodiments, MLA 420 uses numbers between 0 and 1 to determine whether the provided data, e.g., training feature vectors 416, includes a tremor or not. The more data that is provided, the more accurate MLA 420 will be in creating a model, e.g., tremor predictive model 440.

Once MLA 420 creates tremor predictive model 440, test data may be fed into the model to verify the system and test how accurately model 440 behaves. In some embodiments, test data 424 is pre-processed to become a feature vector 436 and passed to tremor predictive model 440 for a prediction. Tremor predictive model 440 identifies if the input test data includes a tremor or not. In some embodiments, each iteration of test data 424 is classified and reviewed for accuracy. For example, if expected label 450 is not correct, false result 452 may be fed back into MLA 420 as learning data. If, after test data 424 is classified and reviewed, model 440 does not perform as expected (e.g., an error rate below 5%) then additional training data may be provided until the model meets the expected criteria. In some embodiments, a reinforcement learning method may be incorporated with test data to reward or punish MLA 420.

Once tremor predictive model 440 works as expected, new real-time data may be fed to the model, and determinations of whether the data includes a tremor may be predicted with confidence. For instance, in scenario 400, new sensor data 430 may pre-processed as a feature vector 436 and passed to tremor predictive model 440 for a prediction. Tremor predictive model 440 may evaluate feature vector 436 and present a label of tremor or no tremor for the data. If new sensor data can be verified outside the system, model 440 may be further updated with feedback and reinforcement for further accuracy.

Figure 5:
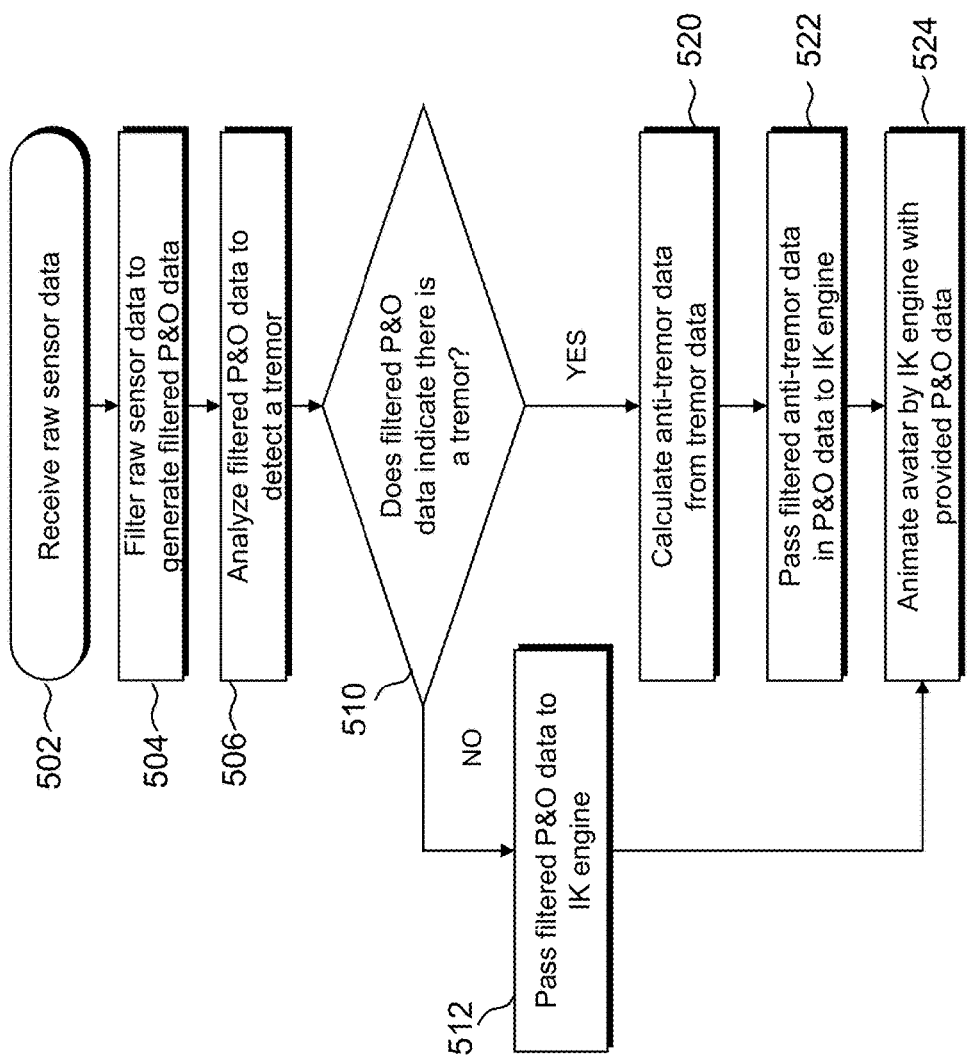
FIG. 5 depicts an illustrative flowchart of a process for identifying a tremor and generating an anti-tremor, in accordance with some embodiments of the disclosure.

FIG. 5 depicts an illustrative flowchart of a process for identifying a tremor and generating an anti-tremor, in accordance with some embodiments of the disclosure. Process 500 includes steps for analyzing data to determine a tremor has occurred and calculating an anti-tremor. Some embodiments may utilize an avatar engine, e.g., as part of a VR application, stored and executed by one or more of the processors and memory of a headset, server, and/or other device carrying out the steps of process 500 depicted in the flowchart of FIG. 5.

At step 502, the avatar engine receives raw sensor data. For example, sensor 202 may measure a relative position and transmit position and orientation (P&O) data to the avatar engine. In some embodiments, sensor 202 may pre-filter or clean "jitter" from raw sensor data prior to transmission. In some embodiments, sensor 202 may capture data at a high frequency (e.g., 200 Hz) and transmit a subset of that data, e.g., transmitting captured data at a lower frequency.

At step 504, the avatar engine filters "raw" sensor data to generate filtered position and orientation data. For instance, the avatar engine may process sensor data to reduce size At step 506, the avatar engine analyzes filtered P&O data to detect a tremor. For instance, the avatar engine may analyze a window of past data to determine if a tremor is occurring in real time. In some embodiments, data may be passed to a neural network, e.g., tremor predictive model 440 as depicted in FIG. 4, for determination if the data includes a tremor.

At step 510, the avatar engine determines if the filtered P&O data indicates there is a tremor. For example, data may be passed to tremor predictive model 440 as depicted in FIG. 4 for classification as to whether the data includes a tremor or not. In some embodiments, tremor data may be identified by oscillations, such as when a body part rotates back and forth. Such oscillations may be identifiable by certain frequencies or amplitudes as measured by the system.

If the avatar engine determines if the filtered P&O data indicates there is a tremor at step 510, the avatar engine calculates anti-tremor data from tremor data at step 520. In some embodiments, anti-tremor data may be calculated by plotting a tremor curve and creating an anti-tremor curve (for all dimensions) as depicted in FIG. 3. In some embodiments, anti-tremor data may be calculated by a process of inverting coordinates, such as the process depicted in FIGS. 6A, 6B, or a combination of the processes. In some embodiments, anti-tremor data may be calculated by a process of inverting rotational data, such as the process depicted in FIG. 6B.

At step 522, the avatar engine passes filtered anti-tremor data in P&O data to the inverse kinematics (IK) engine. For example, the avatar engine may transmit anti-tremor data with other P&O data for rendering by the IK engine depicted in FIG. 9. In some embodiments, the avatar engine must convert the anti-tremor data to data compatible with the P&O data. In some embodiments, the avatar engine replaces the P&O data describing a tremor with P&O data describing an anti-tremor.

If the avatar engine determines if the filtered P&O data indicates there is a tremor at step 510, the avatar engine transmits the filtered P&O data to the IK engine at step 524. For example, the avatar engine may transmit all P&O data for rendering by the IK engine depicted in FIG. 9. In some embodiments, this step occurs the same as if the system were not in anti-tremor mode.

At step 524, the avatar engine animates an avatar with by IK engine with provided P&O data. For instance, if the avatar engine identified a tremor and generated an anti-tremor, the anti-tremor data passed to the IK engine will be used to render and animate an avatar with an anti-tremor. Likewise, if the avatar engine did not identify a tremor, the P&O data is passed to the IK engine and used to render and animate an avatar as per normal conditions (no anti-tremor mode).

FIG. 6A depicts an illustrative flowchart of a process for generating an anti-tremor, in accordance with some embodiments of the disclosure. Process 600 includes steps for calculating an anti-tremor. Some embodiments may utilize an avatar engine, e.g., as part of a VR application, stored and executed by one or more of the processors and memory of a headset, server, and/or other device carrying out the steps of process 600 depicted in the flowchart of FIG. 6A. Process 600 of FIG. 6A may be performed in conjunction with or separately from process 650 depicted in FIG. 6B.

At step 612, the avatar engine receives position and orientation (P&O) data. For instance, the avatar engine may receive raw P&O data from the sensors. In some embodiments, the avatar engine may receive processed or filtered P&O data from the sensors.

At step 614, the avatar engine analyzes P&O data to detect a tremor. For example, data may be passed to tremor predictive model 440 as depicted in FIG. 4 for classification as to whether the data includes a tremor or not. In some embodiments, tremor data may be identified by oscillations, such as when a body part rotates back and forth.

At step 616, the avatar engine establishes a neutral position from sensor data. A neutral state may be a measured sensor position if, e.g., the body part was not experiencing a tremor. For example, the line representing neutral state 312 in FIG. 3 may be considered a neutral position for one axis, e.g., the x-axis. In some embodiments, a neutral position may be calculated based on a weighted average of recent position measurements. In some embodiments, a neutral position may be extrapolated or interpolated from measurements of oscillation. In some embodiments, a neutral position may be identified from measurements of change in acceleration. In some embodiments, a neutral position may be measured and adjusted recursively as displacements of maximum and minimum amplitude may be measured.

At step 618, the avatar engine defines coordinate system with neutral position as the origin. For instance, the line representing neutral state 312 in FIG. 3 would become the x-axis of a new coordinate system, with similar lines for the y-axis and z-axis based on measurements at the time. In some embodiments, a new coordinate system may appear like the coordinate system created by x-axis 252, y-axis 254, and z-axis 256 in FIG. 2.

At step 620, the avatar engine generates a tremor vector from detected tremor data. For instance, a tremor vector may be a measured displacement of a sensor from a neutral position. For instance, displacement vector 260, $\vec{D_1}$, of FIG. 2 represents displacement of real-world hand 110 in the coordinate system of scenario 200 as real-world hand moved to the right-most position. Displacement vector 262, $\vec{D_2}$, of FIG. 2 represents displacement of real-world hand 110 in the coordinate system of scenario 200 as real-world hand moved to the left-most position. In some embodiments, each tremor vector may be generated by the sum of relative measurement of sensor position on each axis, e.g., vector components as depicted by displacement vectors 320A-G in FIG. 3.

At step 622, the avatar engine reflects tremor vector over neutral position to create anti-tremor vector. For example, the avatar engine may reflect a tremor vector over the origin. An anti-tremor vector of displacement vector 262, $\vec{D_2}$, of FIG. 2 would be the same magnitude and opposite direction. In some embodiments, each anti-tremor vector may be generated by the sum of relative measurement of sensor position on each axis, e.g., vector components as depicted by inverse vectors 340B, 340C, and 340E in FIG. 3. In some embodiments only one anti-tremor vector is calculated per iteration. In some embodiments, multiple displacement vectors may be inverted over a neutral state to create multiple anti-tremor vectors for rendering.

At step 624, the avatar engine provides a calculated anti-tremor. In some embodiments, a calculated anti-tremor must be converted, normalized, and/or translated for rendering. In some embodiments, a calculated anti-tremor may be substituted for tremor data and incorporated in P&O data that may be transmitted for rendering and animation.

FIG. 6B depicts an illustrative flowchart of a process for generating an anti-tremor, in accordance with some embodiments of the disclosure. Process 650 includes steps for calculating an anti-tremor. Some embodiments may utilize an avatar engine, e.g., as part of a VR application, stored and executed by one or more of the processors and memory of a headset, server, and/or other device carrying out the steps of process 650 depicted in the flowchart of FIG. 6B. Process 650 of FIG. 6B may be performed in conjunction with or separately from process 600 depicted in FIG. 6A.

At step 662, the avatar engine receives position and orientation (P&O) data. For instance, the avatar engine may receive raw P&O data from the sensors. In some embodiments, the avatar engine may receive processed or filtered P&O data from the sensors.

At step 664, the avatar engine analyzes P&O data to detect a tremor. For example, data may be passed to a neural network, such as tremor predictive model 440 as depicted in FIG. 4 for classification as to whether the data includes a tremor or not. In some embodiments, tremor data may be identified by particular oscillations, such as when a body part rotates back and forth. Such oscillations may be identifiable by certain frequencies or amplitudes as measured by the system.

At step 666, the avatar engine identifies tremor rotation data indicating rotation about one or more axes. For example, orientation data of P&O may be examined for values in one or more of rotation data around three axes.

At step 668, the avatar engine determines inverse of the roll, pitch, and/or yaw of the tremor rotation data. For example, if a tremor causes the body part to rotate 7° to the right around the roll axis (e.g., arrow 124 of FIG. 1), then the inverse rotation would be a rotation of the same magnitude (7°) to the left around the roll axis (e.g., arrow 174 of FIG. 1). By way of another example, if a tremor causes the body part to tilt 10° backwards around the pitch axis (e.g., arrow 128 of FIG. 1), then the inverse rotation would be a rotation of 10° forwards around the pitch axis (e.g., arrow 178 of FIG. 1). For example, if a tremor causes the body part to rotate 5° to the right around the yaw axis (e.g., arrow 134 of FIG. 1), then the inverse rotation would be a rotation 5° to the left around the yaw axis (e.g., arrow 184 of FIG. 1). In some embodiments, the magnitude of the inverse will be the same. In some embodiments, the magnitude of the inverse may be multiplied by a factor.

Some embodiments may receive sensor data indicating multiple rotations and a rotation order must be determined. For instance, a patient may rotate her wrist down towards the palm 45 degrees, and then twist it 45 degrees to the left, which might cause a different orientation, e.g., of a real world wrist or an avatar wrist, than by twisting 45 degrees to the left and then rotating 45 degrees towards the (newly oriented) palm. In such cases, a change of an axis earlier in a rotate order may change the basis of axes later in a rotation order, therefore making an inversion or negation have different effects. In some embodiments, using one sequence of ordered Euler rotations may achieve the same orientation as another sequence of ordered Euler rotations, and Quaternion notation may be used to simplify the rotational information.

At step 670, the avatar engine determines anti-tremor rotation based on the inverse of the roll, pitch, and yaw. In some embodiments, components of rotational data may be summed to produce an angular rotation and direction. In some embodiments, an anti-tremor rotation vector may comprise inverted values of rotation in each of roll, pitch, and yaw.

At step 674, the avatar engine provides a calculated anti-tremor. In some embodiments, a calculated anti-tremor must be converted, normalized, and/or translated for rendering. In some embodiments, a calculated anti-tremor may be substituted for tremor data and incorporated in P&O data that may be transmitted for rendering and animation. For instance, a sensor measurement of rotation in roll, pitch, and yaw may be inverted in direction and incorporated with other data.

An Illustrative Virtual Reality System to Detect Tremors and Render Anti-Tremors Disclosed herein is an illustrative medical device system including a virtual reality (VR) system to enable therapy for a patient. Such a VR medical device system may include a headset, sensors, a therapist tablet, among other hardware to enable games and activities to train (or retrain) a patient's body movements.

As described herein, VR systems capable for use in physical therapy may be tailored to be durable, portable and allow for quick and consistent setup. In some embodiments, a virtual reality system for therapy may be a modified commercial VR system using, e.g., a headset and several body sensors configured for wireless communication. A VR system capable of use for therapy may need to collect patient movement data. In some embodiments, sensors, placed on the patient's body, can translate patient body movement to the VR system for animation of a VR avatar. Sensor data may also be used to measure patient movement and determine motion for patient body parts.

Figure 7B:
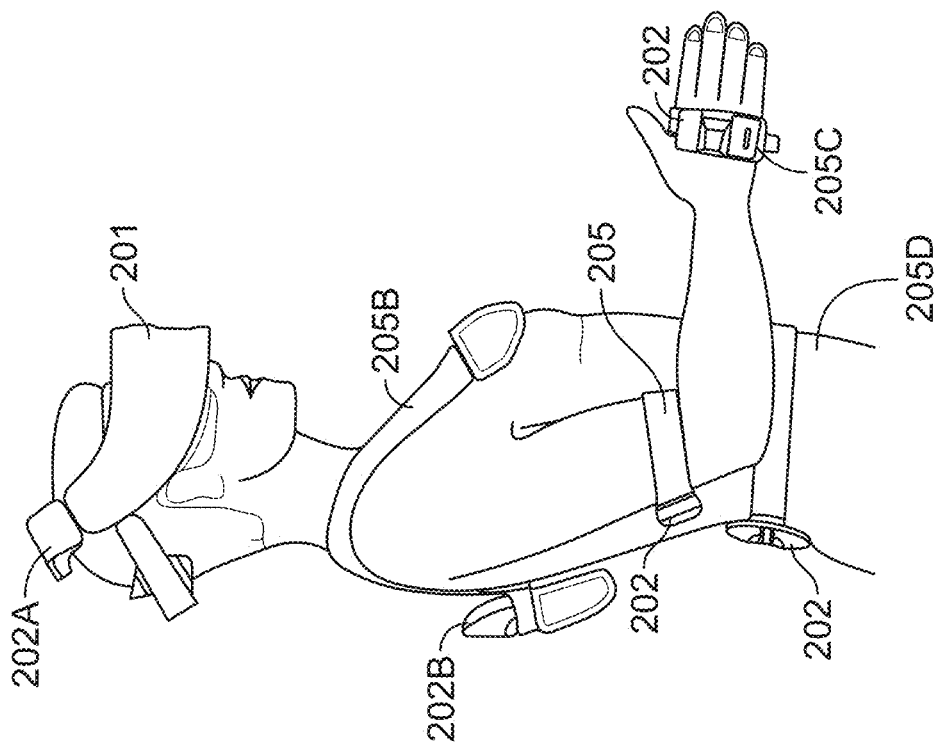
FIG. 7B is a diagram of an illustrative system, in accordance with some embodiments of the disclosure.
Figure 7A:
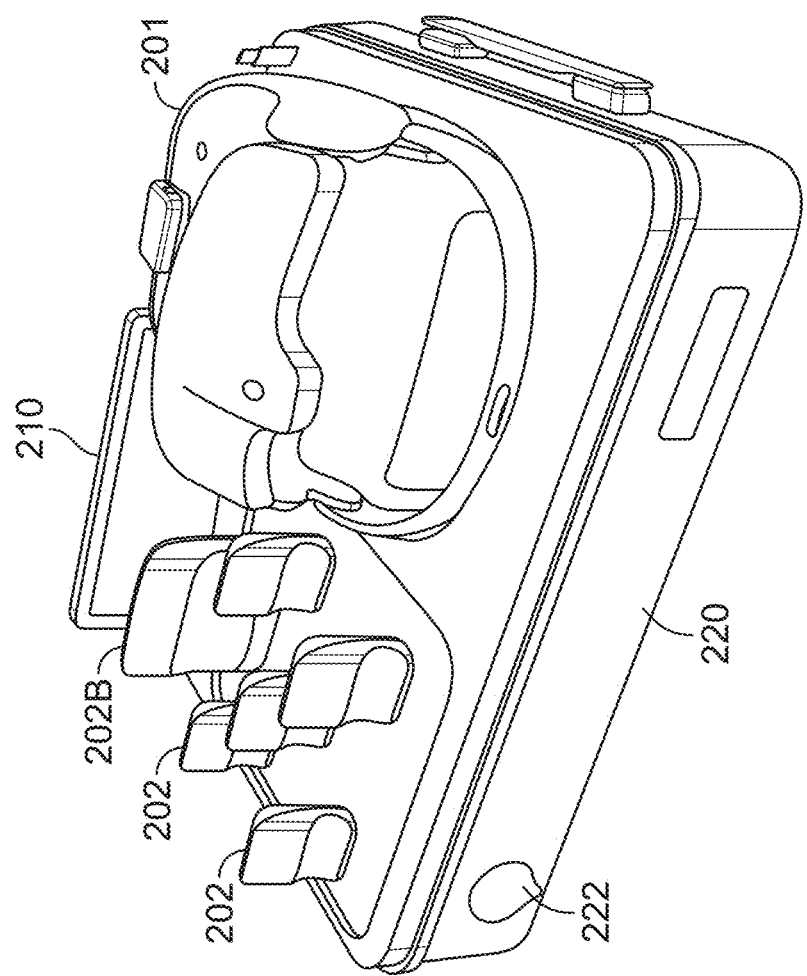
FIG. 7A is a diagram of an illustrative system, in accordance with some embodiments of the disclosure.
Figure 7D:
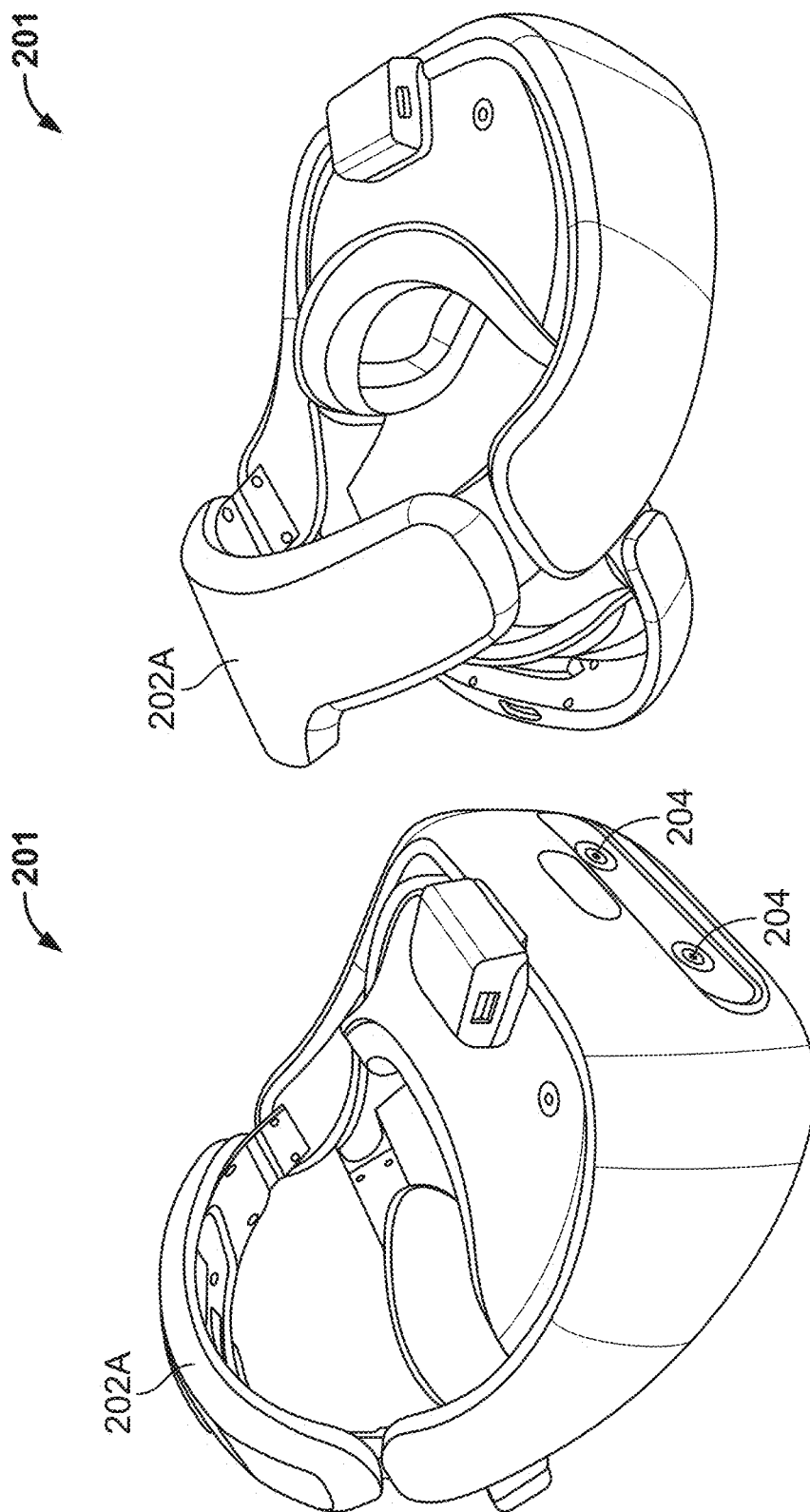
FIG. 7D is a diagram of an illustrative system, in accordance with some embodiments of the disclosure.

FIG. 7A is a diagram of an illustrative system, in accordance with some embodiments of the disclosure. A VR system may include a clinician tablet 210, head-mounted display 201 (HMD or headset), small sensors 202, and large sensor 202B. Large sensor 202B may comprise transmitters, in some embodiments, and be referred to as wireless transmitter module 202B. Some embodiments may include sensor chargers, router, router battery, headset controller, power cords, USB cables, and other VR system equipment.

Clinician tablet 210 may be configured to use a touch screen, a power/lock button that turns the component on or off, and a charger/accessory port, e.g., USB-C. For instance, pressing the power button on clinician tablet 210 may power on the tablet or restart the tablet. Once clinician tablet 210 is powered on, a therapist or supervisor may access a user interface and be able to log in; add or select a patient; initialize and sync sensors; select, start, modify, or end a therapy session; view data; and/or log out.

Headset 201 may comprise a power button that turns the component on or off, as well as a charger/accessory port, e.g., USB-C. Headset 201 may also provide visual feedback of virtual reality applications in concert with the clinician tablet and the small and large sensors.

Charging headset 201 may be performed by plugging a headset power cord into the storage dock or an outlet. To turn on headset 201 or restart headset 201, the power button may be pressed. A power button may be on top of the headset. Some embodiments may include a headset controller used to access system settings. For instance, a headset controller may be used only in certain troubleshooting and administrative tasks and not necessarily during patient therapy. Buttons on the controller may be used to control power, connect to headset 201, access settings, or control volume.

The large sensor 202B and small sensors 202 are equipped with mechanical and electrical components that measure position and orientation in physical space and then translate that information to construct a virtual environment. Sensors 202 are turned off and charged when placed in the charging station. Sensors 202 turn on and attempt to sync when removed from the charging station. The sensor charger acts as a dock to store and charge the sensors. In some embodiments, sensors may be placed in sensor bands on a patient. Sensor bands 205, as depicted in FIGS. 7B-C, are typically required for use and are provided separately for each patient for hygienic purposes. In some embodiments, sensors may be miniaturized and may be placed, mounted, fastened, or pasted directly onto a user.

As shown in illustrative FIG. 7A, various systems disclosed herein consist of a set of position and orientation sensors that are worn by a VR participant, e.g., a therapy patient. These sensors communicate with HMD 201, which immerses the patient in a VR experience. An HMD suitable for VR often comprises one or more displays to enable stereoscopic three-dimensional (3D) images. Such internal displays are typically high-resolution (e.g., 2880×1600 or better) and offer high refresh rate (e.g., 75 Hz). The displays are configured to present 3D images to the patient. VR headsets typically include speakers and microphones for deeper immersion.

HMD 201 is a piece central to immersing a patient in a virtual world in terms of presentation and movement. A headset may allow, for instance, a wide field of view (e.g., 110°) and tracking along six degrees of freedom. HMD 201 may include cameras, accelerometers, gyroscopes, and proximity sensors. VR headsets typically include a processor, usually in the form of a system on a chip (SoC), and memory. In some embodiments, headsets may also use, for example, additional cameras as safety features to help users avoid real-world obstacles. HMD 201 may comprise more than one connectivity option in order to communicate with the therapist's tablet. For instance, an HMD 201 may use an SoC that features WiFi and Bluetooth connectivity, in addition to an available USB connection (e.g., USB Type-C). The USB-C connection may also be used to charge the built-in rechargeable battery for the headset.

A supervisor, such as a health care provider or therapist, may use a tablet, e.g., tablet 210 depicted in FIG. 7A, to control the patient's experience. In some embodiments, tablet 210 runs an application and communicates with a router to cloud software configured to authenticate users and store information. Tablet 210 may communicate with HMD 201 in order to initiate HMD applications, collect relayed sensor data, and update records on the cloud servers. Tablet 210 may be stored in the portable container and plugged in to charge, e.g., via a USB plug.

In some embodiments, such as depicted in FIGS. 7B-C, sensors 202 are placed on the body in particular places to measure body movement and relay the measurements for translation and animation of a VR avatar. Sensors 202 may be strapped to a body via bands 205. In some embodiments, each patient may have her own set of bands 205 to minimize hygiene issues.

A wireless transmitter module (WTM) 202B may be worn on a sensor band 205B that is laid over the patient's shoulders. WTM 202B sits between the patient's shoulder blades on their back. Wireless sensor modules 202 (e.g., sensors or WSMs) are worn just above each elbow, strapped to the back of each hand, and on a pelvis band that positions a sensor adjacent to the patient's sacrum on their back. In some embodiments, each WSM communicates its position and orientation in real-time with an HMD Accessory located on the HMD. Each sensor 202 may learn its relative position and orientation to the WTM, e.g., via calibration.

The HMD accessory may include a sensor 202A that may allow it to learn its position relative to WTM 202B, which then allows the HMD to know where in physical space all the WSMs and WTM are located. In some embodiments, each sensor 202 communicates independently with the HMD accessory which then transmits its data to HMD 201, e.g., via a USB-C connection. In some embodiments, each sensor 202 communicates its position and orientation in real-time with WTM 202B, which is in wireless communication with HMD 201.

A VR environment rendering engine on HMD 201 (sometimes referred to herein as a "VR application"), such as the Unreal Engine™, uses the position and orientation data to create an avatar that mimics the patient's movement.

A patient or player may "become" their avatar when they log in to a virtual reality game. When the player moves their body, they see their avatar move accordingly. Sensors in the headset may allow the patient to move the avatar's head, e.g., even before body sensors are placed on the patient. A system that achieves consistent high-quality tracking facilitates the patient's movements to be accurately mapped onto an avatar.

Sensors 202 may be placed on the body, e.g., of a patient by a therapist, in particular locations to sense and/or translate body movements. The system can use measurements of position and orientation of sensors placed in key places to determine movement of body parts in the real world and translate such movement to the virtual world. In some embodiments, a VR system may collect data for therapeutic analysis of a patient's movements and range of motion.

In some embodiments, systems and methods of the present disclosure may use electromagnetic tracking, optical tracking, infrared tracking, accelerometers, magnetometers, gyroscopes, myoelectric tracking, other tracking techniques, or a combination of one or more of such tracking methods. The tracking systems may be parts of a computing system as disclosed herein. The tracking tools may exist on one or more circuit boards within the VR system (see FIG. 9) where they may monitor one or more users to perform one or more functions such as capturing, analyzing, and/or tracking a subject's movement. In some cases, a VR system may utilize more than one tracking method to improve reliability, accuracy, and precision.

Figure 8A:
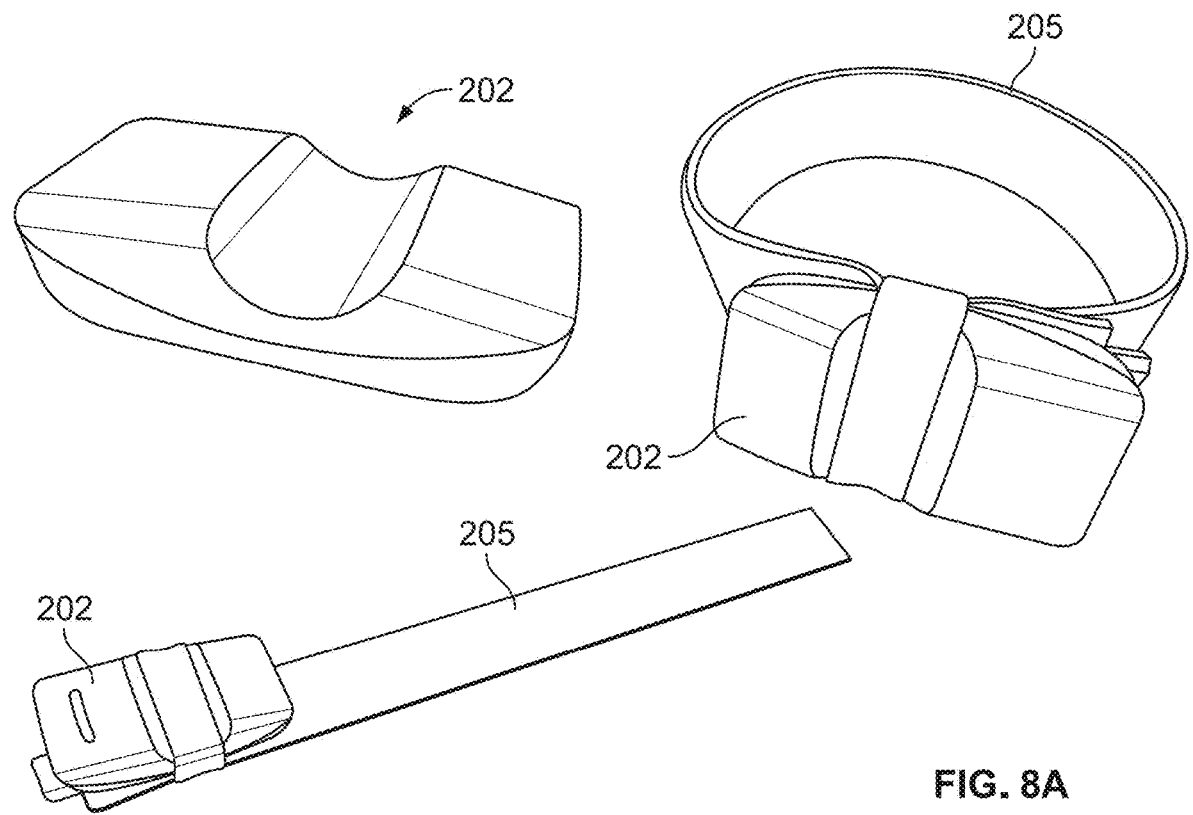
FIG. 8A is a diagram of an illustrative system, in accordance with some embodiments of the disclosure.
Figure 8B:
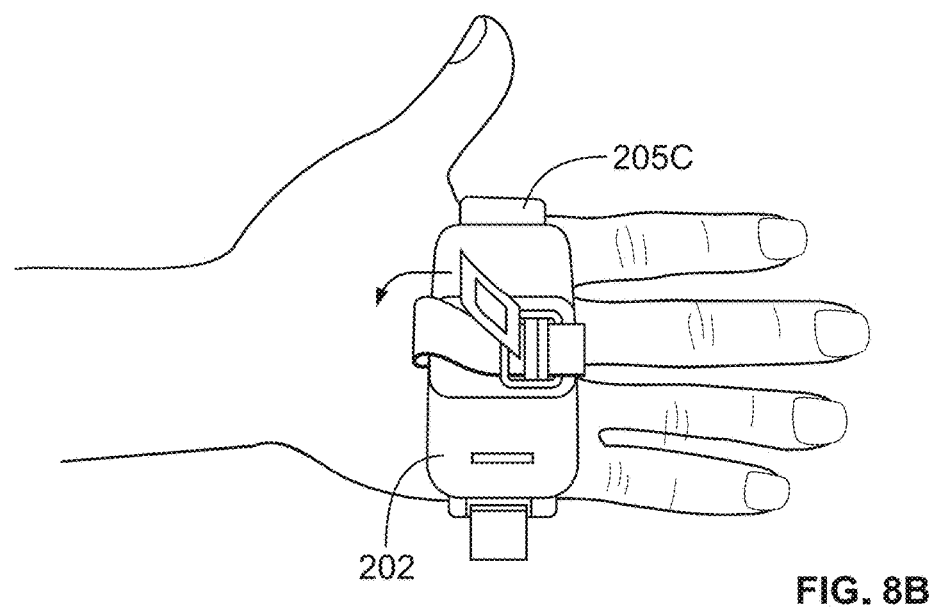
FIG. 8B is a diagram of an illustrative system, in accordance with some embodiments of the disclosure.
Figure 8C:
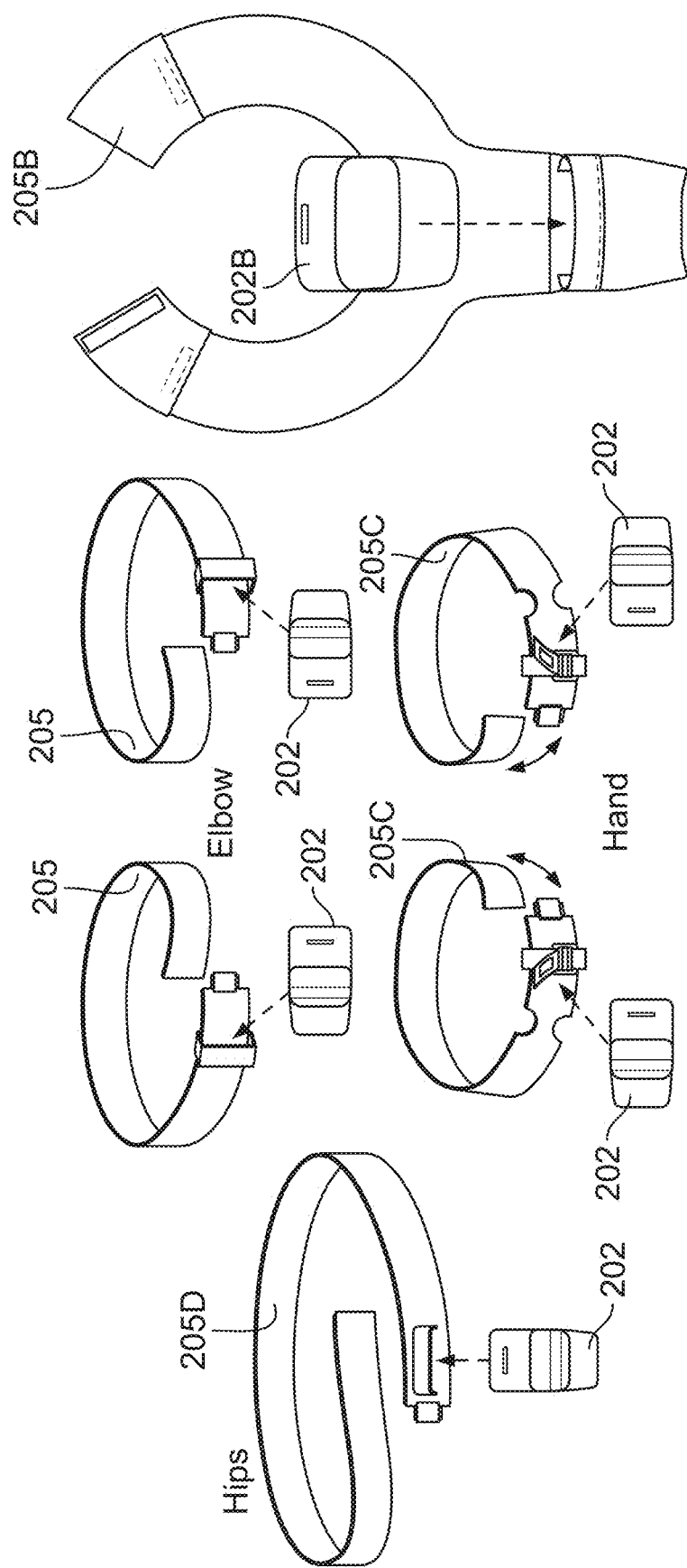
FIG. 8C is a diagram of an illustrative system, in accordance with some embodiments of the disclosure.

FIGS. 8A-C illustrate examples of wearable sensors 202 and bands 205. In some embodiments, bands 205 may include elastic loops to hold the sensors. In some embodiments, bands 205 may include additional loops, buckles and/or Velcro straps to hold the sensors. For instance, bands 205 for hands may require extra secureness as a patient's hands may be moved at a greater speed and could throw or project a sensor in the air if it is not securely fastened. FIG. 2C illustrates an exemplary embodiment with a slide buckle.

Sensors 202 may be attached to body parts via band 205. In some embodiments, a therapist attaches sensors 202 to proper areas of a patient's body. For example, a patient may not be physically able to attach band 205 to herself. In some embodiments, each patient may have her own set of bands 205 to minimize hygiene issues. In some embodiments, a therapist may bring a portable case to a patient's room or home for therapy. The sensors may include contact ports for charging each sensor's battery while storing and transporting in the container, such as the container depicted in FIG. 7A.

As illustrated in FIG. 8C, sensors 202 are placed in bands 205 prior to placement on a patient. In some embodiments, sensors 202 may be placed onto bands 205 by sliding them into the elasticized loops. The large sensor, WTM 202B, is placed into a pocket of shoulder band 205B. Sensors 202 may be placed above the elbows, on the back of the hands, and at the lower back (sacrum). In some embodiments, sensors may be used at the knees and/or ankles. Sensors 202 may be placed, e.g., by a therapist, on a patient while the patient is sitting on a bench (or chair) with his hands on his knees. Sensor band 205D to be used as a hip sensor 202 has a sufficient length to encircle a patient's waist.

Once sensors 202 are placed in bands 205, each band may be placed on a body part, e.g., according to FIG. 7C. In some embodiments, shoulder band 205B may require connection of a hook and loop fastener. An elbow band 205 holding a sensor 202 should sit behind the patient's elbow. In some embodiments, hand sensor bands 205C may have one or more buckles to, e.g., fasten sensors 202 more securely, as depicted in FIG. 8B.

Each of sensors 202 may be placed at any of the suitable locations, e.g., as depicted in FIG. 7C. After sensors 202 have been placed on the body, they may be assigned or calibrated for each corresponding body part.

Generally, sensor assignment may be based on the position of each sensor 202. Sometimes, such as cases where patients have varying height discrepancies, assigning a sensor merely based on height is not practical. In some embodiments, sensor assignment may be based on relative position to, e.g., wireless transmitter module 202B.

Figure 9:
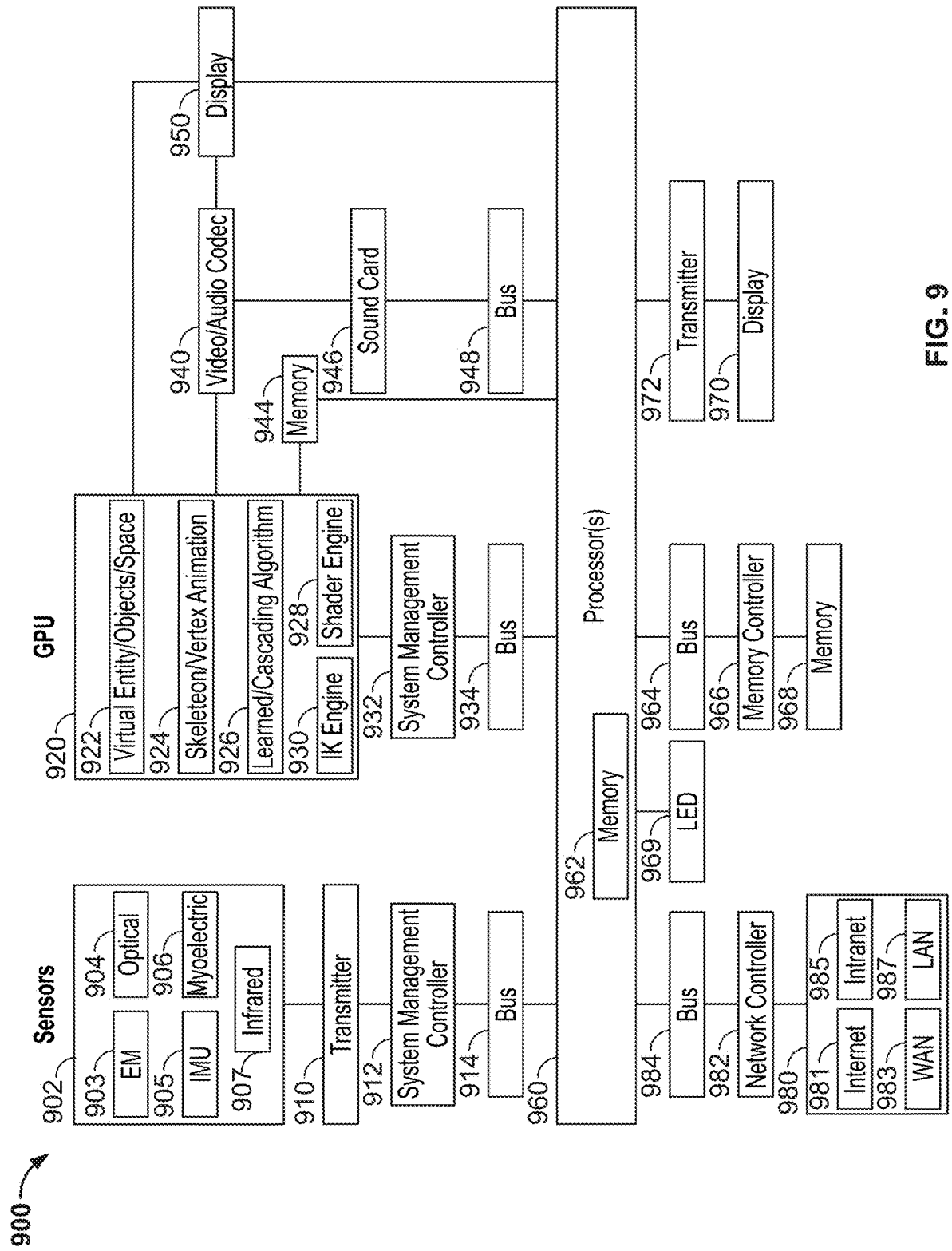
FIG. 9 is a diagram of an illustrative system, accordance with some embodiments of the disclosure.

FIG. 9 depicts an illustrative arrangement for various elements of a system, e.g., an HMD and sensors of FIGS. 7A-D. The arrangement includes one or more printed circuit boards (PCBs). In general terms, the elements of this arrangement track, model, and display a visual representation of the participant (e.g., a patient avatar) in the VR world by running software including the aforementioned VR application of HMD 201.

The arrangement shown in FIG. 9 includes one or more sensors 902, processors 960, graphic processing units (GPUs) 920, video encoder/video codec 940, sound cards 946, transmitter modules 910, network interfaces 980, and light emitting diodes (LEDs) 969. These components may be housed on a local computing system or may be remote components in wired or wireless connection with a local computing system (e.g., a remote server, a cloud, a mobile device, a connected device, etc.). Connections between components may be facilitated by one or more buses, such as bus 914, bus 934, bus 948, bus 984, and bus 964 (e.g., peripheral component interconnects (PCI) bus, PCI-Express bus, or universal serial bus (USB)). With such buses, the computing environment may be capable of integrating numerous components, numerous PCBs, and/or numerous remote computing systems.

One or more system management controllers, such as system management controller 912 or system management controller 932, may provide data transmission management functions between the buses and the components they integrate. For instance, system management controller 912 provides data transmission management functions between bus 914 and sensors 902. System management controller 932 provides data transmission management functions between bus 934 and GPU 920. Such management controllers may facilitate the arrangements orchestration of these components that may each utilize separate instructions within defined time frames to execute applications. Network interface 980 may include an ethernet connection or a component that forms a wireless connection, e.g., 802.11b, g, a, or n connection (WiFi), to a local area network (LAN) 987, wide area network (WAN) 983, intranet 985, or internet 981. Network controller 982 provides data transmission management functions between bus 984 and network interface 980.

Processor(s) 960 and GPU 920 may execute a number of instructions, such as machine-readable instructions. The instructions may include instructions for receiving, storing, processing, and transmitting tracking data from various sources, such as electromagnetic (EM) sensors 903, optical sensors 904, infrared (IR) sensors 907, inertial measurement units (IMUs) sensors 905, and/or myoelectric sensors 906. The tracking data may be communicated to processor(s) 960 by either a wired or wireless communication link, e.g., transmitter 910. Upon receiving tracking data, processor(s) 960 may execute an instruction to permanently or temporarily store the tracking data in memory 962 such as, e.g., random access memory (RAM), read only memory (ROM), cache, flash memory, hard disk, or other suitable storage component. Memory may be a separate component, such as memory 968, in communication with processor(s) 960 or may be integrated into processor(s) 960, such as memory 962, as depicted.

Processor(s) 960 may also execute instructions for constructing an instance of virtual space. The instance may be hosted on an external server and may persist and undergo changes even when a participant is not logged in to said instance. In some embodiments, the instance may be participant-specific, and the data required to construct it may be stored locally. In such an embodiment, new instance data may be distributed as updates that users download from an external source into local memory. In some exemplary embodiments, the instance of virtual space may include a virtual volume of space, a virtual topography (e.g., ground, mountains, lakes), virtual objects, and virtual characters (e.g., non-player characters "NPCs"). The instance may be constructed and/or rendered in 2D or 3D. The rendering may offer the viewer a first-person or third-person perspective. A first-person perspective may include displaying the virtual world from the eyes of the avatar and allowing the patient to view body movements from the avatar's perspective. A third-person perspective may include displaying the virtual world from, for example, behind the avatar to allow someone to view body movements from a different perspective. The instance may include properties of physics, such as gravity, magnetism, mass, force, velocity, and acceleration, which cause the virtual objects in the virtual space to behave in a manner at least visually similar to the behaviors of real objects in real space.

Processor(s) 960 may execute a program (e.g., the Unreal Engine or VR applications discussed above) for analyzing and modeling tracking data. For instance, processor(s) 960 may execute a program that analyzes the tracking data it receives according to algorithms described above, along with other related pertinent mathematical formulas. Such a program may incorporate a graphics processing unit (GPU) 920 that is capable of translating tracking data into 3D models. GPU 920 may utilize shader engine 928, vertex animation 924, and linear blend skinning algorithms. In some instances, processor(s) 960 or a CPU may at least partially assist the GPU in making such calculations. This allows GPU 920 to dedicate more resources to the task of converting 3D scene data to the projected render buffer. GPU 920 may refine the 3D model by using one or more algorithms, such as an algorithm learned on biomechanical movements, a cascading algorithm that converges on a solution by parsing and incrementally considering several sources of tracking data, an inverse kinematics (IK) engine 930, a proportionality algorithm, and other algorithms related to data processing and animation techniques. After GPU 920 constructs a suitable 3D model, processor(s) 960 executes a program to transmit data for the 3D model to another component of the computing environment (or to a peripheral component in communication with the computing environment) that is capable of displaying the model, such as display 950.

In some embodiments, GPU 920 transfers the 3D model to a video encoder or a video codec 940 via a bus, which then transfers information representative of the 3D model to a suitable display 950. The 3D model may be representative of a virtual entity that can be displayed in an instance of virtual space, e.g., an avatar. The virtual entity is capable of interacting with the virtual topography, virtual objects, and virtual characters within virtual space. The virtual entity is controlled by a user's movements, as interpreted by sensors 902 communicating with the system. Display 950 may display a Patient View. The patient's real-world movements are reflected by the avatar in the virtual world. The virtual world may be viewed in the headset in 3D and monitored on the tablet in two dimensions. In some embodiments, the VR world is a game that provides feedback and rewards based on the patient's ability to complete activities. Data from the in-world avatar is transmitted from the HMD to the tablet to the cloud, where it is stored for later analysis. An illustrative architectural diagram of such elements in accordance with some embodiments is depicted in FIG. 10.

A VR system may also comprise display 970, which is connected to the computing environment via transmitter 972. Display 970 may be a component of a clinician tablet. For instance, a supervisor or operator, such as a therapist, may securely log in to a clinician tablet, coupled to the system, to observe and direct the patient to participate in various activities and adjust the parameters of the activities to best suit the patient's ability level. Display 970 may depict a view of the avatar and/or replicate the view of the HMD.

Figure 10:
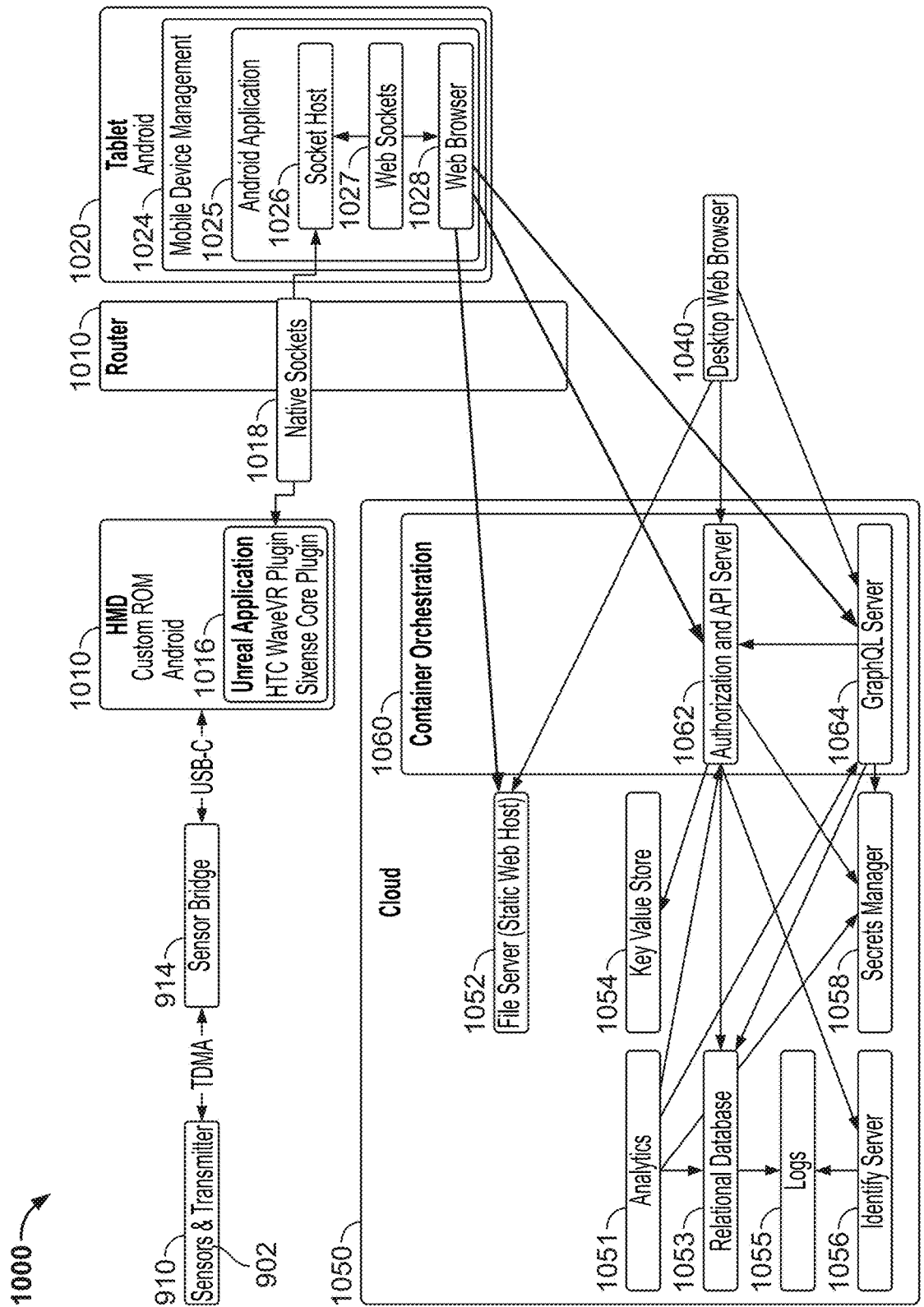
FIG. 10 is a diagram of an illustrative system, in accordance with some embodiments of the disclosure.

In some embodiments, HMD 201 may be the same as or similar to HMD 1010 in FIG. 10. In some embodiments, HMD 1010 runs a version of Android that is provided by HTC (e.g., a headset manufacturer) and the VR application is an Unreal application, e.g., Unreal Application 1016, encoded in an Android package (.apk). The .apk comprises a set of custom plugins: WVR, WaveVR, SixenseCore, SixenseLib, and MVICore. The WVR and WaveVR plugins allow the Unreal application to communicate with the VR headset's functionality. The SixenseCore, SixenseLib, and MVICore plugins allow Unreal Application 1016 to communicate with the HMD accessory and sensors that communicate with the HMD via USB-C. The Unreal Application comprises code that records the position and orientation (P&O) data of the hardware sensors and translates that data into a patient avatar, which mimics the patient's motion within the VR world. An avatar can be used, for example, to infer and measure the patient's real-world range of motion. The Unreal application of the HMD includes an avatar solver as described, for example, below.

The operator device, clinician tablet 1020, runs a native application (e.g., Android application 1025) that allows an operator such as a therapist to control a patient's experience. Cloud server 1050 includes a combination of software that manages authentication, data storage and retrieval, and hosts the user interface, which runs on the tablet. This can be accessed by tablet 1020. Tablet 1020 has several modules.

As depicted in FIG. 10, the first part of tablet software is a mobile device management (MDM) 1024 layer, configured to control what software runs on the tablet, enable/disable the software remotely, and remotely upgrade the tablet applications.

The second part is an application, e.g., Android Application 1025, configured to allow an operator to control the software of HMD 1010. In some embodiments, the application may be a native application. A native application, in turn, may comprise two parts, e.g., (1) socket host 1026 configured to receive native socket communications from the HMD and translate that content into web sockets, e.g., web sockets 1027, that a web browser can easily interpret; and (2) a web browser 1028, which is what the operator sees on the tablet screen. The web browser may receive data from the HMD via the socket host 1026, which translates the HMD's native socket communication 1018 into web sockets 1027, and it may receive UI/UX information from a file server 1052 in cloud 1050. Tablet 1020 comprises web browser 1028, which may incorporate a real-time 3D engine, such as Babylon.js, using a JavaScript library for displaying 3D graphics in web browser 1028 via HTML5. For instance, a real-time 3D engine, such as Babylon.js, may render 3D graphics, e.g., in web browser 1028 on clinician tablet 1020, based on received skeletal data from an avatar solver in the Unreal Engine 1016 stored and executed on HMD 1010. In some embodiments, rather than Android Application 1026, there may be a web application or other software to communicate with file server 1052 in cloud 1050. In some instances, an application of Tablet 1020 may use, e.g., Web Real-Time Communication (WebRTC) to facilitate peer-to-peer communication without plugins, native apps, and/or web sockets.

The cloud software, e.g., cloud 1050, has several different, interconnected parts configured to communicate with the tablet software: authorization and API server 1062, GraphQL server 1064, and file server (static web host) 1052.

In some embodiments, authorization and API server 1062 may be used as a gatekeeper. For example, when an operator attempts to log in to the system, the tablet communicates with the authorization server. This server ensures that interactions (e.g., queries, updates, etc.) are authorized based on session variables such as operator's role, the health care organization, and the current patient. This server, or group of servers, communicates with several parts of the system: (a) a key value store 1054, which is a clustered session cache that stores and allows quick retrieval of session variables; (b) a GraphQL server 1064, as discussed below, which is used to access the back-end database in order to populate the key value store, and also for some calls to the application programming interface (API); (c) an identity server 1056 for handling the user login process; and (d) a secrets manager 1058 for injecting service passwords (relational database, identity database, identity server, key value store) into the environment in lieu of hard coding.

When the tablet requests data, it will communicate with the GraphQL server 1064, which will, in turn, communicate with several parts: (1) the authorization and API server 1062; (2) the secrets manager 1058, and (3) a relational database 1053 storing data for the system. Data stored by the relational database 1053 may include, for instance, profile data, session data, game data, and motion data.

In some embodiments, profile data may include information used to identify the patient, such as a name or an alias. Session data may comprise information about the patient's previous sessions, as well as, for example, a "free text" field into which the therapist can input unrestricted text, and a log 1055 of the patient's previous activity. Logs 1055 are typically used for session data and may include, for example, total activity time, e.g., how long the patient was actively engaged with individual activities; activity summary, e.g., a list of which activities the patient performed, and how long they engaged with each on; and settings and results for each activity. Game data may incorporate information about the patient's progression through the game content of the VR world. Motion data may include specific range-of-motion (ROM) data that may be saved about the patient's movement over the course of each activity and session, so that therapists can compare session data to previous sessions' data.

In some embodiments, file server 1052 may serve the tablet software's website as a static web host.

While the foregoing discussion describes exemplary embodiments of the present invention, one skilled in the art will recognize from such discussion, the accompanying drawings, and the claims, that various modifications can be made without departing from the spirit and scope of the invention. Therefore, the illustrations and examples herein should be construed in an illustrative, and not a restrictive sense. The scope and spirit of the invention should be measured solely by reference to the claims that follow.

What is claimed is:

1. A method for detecting and rendering tremors in a virtual reality environment, the method comprising:
   receiving raw sensor data;
   filtering the raw sensor data to generate filtered position and orientation data;
   determining whether the filtered position and orientation data describes a tremor comprising a tremor frequency and a tremor amplitude;
   in response to determining the filtered position and orientation data describes the tremor, calculating an anti-tremor based on the filtered position and orientation data; and
   rendering an avatar based on the anti-tremor, wherein the avatar is displayed in the virtual reality environment in motion due to the anti-tremor, and wherein the anti-tremor comprises an anti-tremor frequency equal to the tremor frequency and an anti-tremor amplitude that is opposite in amplitude to the tremor amplitude.

2. The method of claim 1, wherein the determining uses a trained machine learning model to determine whether the filtered position and orientation data comprises data describing the tremor.

3. The method of claim 2, wherein the trained machine learning model is trained to receive position and orientation data and output a determination whether the filtered position and orientation data comprises data describing the tremor.

4. The method of claim 2, wherein the trained machine learning model is trained to receive position and orientation data and output which portion of the filtered position and orientation data comprises data describing the tremor.

5. The method of claim 1, wherein the determining uses a data analytics technique to determine whether the filtered position and orientation data comprises data describing the tremor.

6. The method of claim 5, wherein using the data analytics technique comprises processing position and orientation data to identify at least one of the following: oscillation, rotation, rhythm, pattern, and change in acceleration.

7. The method of claim 1, wherein calculating an anti-tremor comprises performing at least one of the following to the data describing the tremor: inverting, translating, transposing, transforming, and scaling.

8. The method of claim 1, wherein calculating an anti-tremor comprises:
   establishing a neutral position based on the filtered position and orientation data;
   defining a coordinate system based on the neutral position;
   determining a tremor vector in the coordinate system based on the filtered position and orientation data describing the tremor; and
   determining an anti-tremor vector based on a reflection of the tremor vector over the neutral position in the coordinate system.

9. The method of claim 1, wherein calculating an anti-tremor comprises:
   determining tremor rotation data based on the filtered position and orientation data describing the tremor; and
   determining anti-tremor vector rotation data based on inverting tremor rotation data.

10. The method of claim 1, wherein filtering comprises using at least one of the following: a feature extraction technique, a noise-reduction technique, signal processing, transforming, and normalizing.

11. The method of claim 1, wherein rendering the avatar based on the anti-tremor comprises:
    substituting the filtered position and orientation data describing the tremor with data describing the anti-tremor; and
    rendering the avatar based on the filtered position and orientation data with the substituted data describing the anti-tremor.

12. The method of claim 1, wherein receiving raw sensor data is received wirelessly.

13. The method of claim 1, wherein receiving raw sensor data is received from a plurality of sensors placed on a patient's body.

14. The method of claim 1, wherein filtering the raw sensor data is performed by a plurality of sensors placed on a patient's body.

15. The method of claim 1, wherein rendering the avatar is performed in near real time with receiving the raw sensor data.

16. A system of detecting and rendering tremors in a virtual reality environment, the system comprising:
    a receiver configured to receive raw sensor data;
    processing circuitry configured to:
      filter the raw sensor data to generate filtered position and orientation data;
      determine whether the filtered position and orientation data describes a tremor comprising a tremor frequency and a tremor amplitude;
      in response to determining the filtered position and orientation data describes the tremor, calculate an anti-tremor based on the filtered position and orientation data; and
      render an avatar based on the anti-tremor, wherein the avatar is displayed in the virtual reality environment in motion due to the anti-tremor, and wherein the anti-tremor comprises an anti-tremor frequency equal to the tremor frequency and an anti-tremor amplitude that is opposite in amplitude to the tremor amplitude.

17. The system of claim 16, wherein the processing circuitry is further configured to determine using a trained machine learning model to determine whether the filtered position and orientation data comprises data describing the tremor.

18. The system of claim 17, wherein the trained machine learning model is trained to receive position and orientation data and output a determination whether the filtered position and orientation data comprises data describing the tremor.

19. The system of claim 17, wherein the trained machine learning model is trained to receive position and orientation data and output which portion of the filtered position and orientation data comprises data describing the tremor.

20. The system of claim 16, wherein the processing circuitry is further configured to determine using a data analytics technique to determine whether the filtered position and orientation data comprises data describing the tremor.

\* \* \* \* \*